(12) United States Patent
Moore

(10) Patent No.: US 9,243,280 B2
(45) Date of Patent: Jan. 26, 2016

(54) CELLULAR DEPLETION OF BIOMOLECULAR TARGETS

(75) Inventor: Sean D. Moore, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 79 days.

(21) Appl. No.: 13/403,788

(22) Filed: Feb. 23, 2012

(65) Prior Publication Data

US 2012/0214170 A1    Aug. 23, 2012

Related U.S. Application Data

(60) Provisional application No. 61/445,648, filed on Feb. 23, 2011.

(51) Int. Cl.
*C12Q 1/37*    (2006.01)

(52) U.S. Cl.
CPC ....................................... *C12Q 1/37* (2013.01)

(58) Field of Classification Search
CPC .................................................... C07K 14/00
See application file for complete search history.

(56) References Cited

PUBLICATIONS

Farrell et al., Molecular Micorbiology, 2005, vol. 57, pp. 1750-1761.*
Zhang et al., Nature Biotechnology, 2000, vol. 18, pp. 1314-1317.*
Gottesman et al., Genes & Development, 1998, vol. 12, pp. 1338-1347.*
Sengupta et al., PNAS, 2001, vol. 98, pp. 11991-11996.*
Ahlawat et al., Journal of Bacteriology, 2009, vol. 191, pp. 2894-2898.*
Flynn et al., PNAS, 2001, vol. 98 pp. 10584-10589.*
U.S. Appl. No. 61/445,648, filed Feb. 23, 2011, Sean D. Moore.
Abo T, et al. (2000) SsrA-mediated tagging and proteolysis of LadI and its role in the regulation of lac operon. EMBO J. 19:3762-3769.
Akiyama Y (2009) Quality control of cytoplasmic membrane proteins in *Escherichia coli*. Biochem J. 146:449-454.
Altuvia S (2007) Identification of bacterial small non-coding RNAs: experimental approaches. Curr Opin Microbiol J. 10:257-261.
Arraiano C.M., et al. (2010) The critical role of RNA processing and degradation in the control of gene expression. FEMS Microbiol Rev J. 34:883-923.
Baba T., et al. (2006) Construction of *Escherichia coli* K-12 in-frame, single-gene knockout mutants: the Keio collection. Mol Syst Biol J. 2:2006.0008.
Baker T.A., et al. (2006) ATP-dependent proteases of bacteria: recognition logic and operating principles. Trends Biochem Sci J. 31:647-653.
Baker T.A., et al. (2011) ClpXP, an ATP-powered unfolding and protein-degradation machine. Biochim Biophys Acta. 1823:15-28.
Bernstein J.A., et al. (2002) Global analysis of mRNA decay and abundance in *Escherichia coli* at single-gene resolution using two-color fluorescent DNA microarrays. Proc Natl Acad Sci U S A J. 99:9697-9702.
Boileau G., et al. (1981) Identification of proteins at the binding site for protein S1 in 70 S ribosomes and 30 S subunits by cross-linking with 2-iminothiolane. Biol Chem J. 256:8222-8227.
Bolon D.N., et al. (2004) Nucleotide-dependent substrate handoff from the SspB adaptor to the AAA+ ClpXP protease. Mol Cell J. 16:343-350.
Boni I.V., et al. (2000) The last RNA-binding repeat of the *Escherichia coli* ribosomal protein S1 is specifically involved in autogenous control. Bacteriol J. 182:5872-5879.
Boni I.V., et al. (1991) Ribosome-messenger recognition: mRNA target sites for ribosomal protein S1. Nucleic Acids Res J. 19:155-162.
Briani F., et al. (2008) Polynucleotide phosphorylase hinders mRNA degradation upon ribosomal protein S1 overexpression in *Escherichia coli*. RNA J. 14:2417-2429.
Britton R.A. (2009) Role of GTPases in bacterial ribosome assembly. Annu Rev Microbiol J. 63:155-176.
Brock J.E., et al. (2008) Ribosomes bind leaderless mRNA in *Escherichia coli* through recognition of their 5'-terminal AUG. RNA J. 14:2159-2169.
Burger A., et al. (2011) Current perspectives of the *Escherichia coli* RNA degradosome. Biotechnol Lett J. 33:2337-2350.
Charpentier B., et al. (1994) The *Escherichia coli* gapA gene is transcribed by the vegetative RNA polymerase holoenzyme E sigma 70 and by the heat shock RNA polymerase E sigma 32. J Bacteriol J. 176:830-839.
Cho B.K., et al. (2009) The transcription unit architecture of the *Escherichia coli* genome. Nat Biotechnol J. 27:1043-1049.
Condon C. (2006) Shutdown decay of mRNA. Mol Microbiol J. 61:573-583.
Connolly K. (2008) Mechanistic insight into the ribosome biogenesis functions of the ancient protein KsgA. Mol Microbiol J. 70:1062-1075.
Conrad T.M., et al. (2009) Whole-genome resequencing of *Escherichia coli* K-12 MG1655 undergoing short-term laboratory evolution in lactate minimal media reveals flexible selection of adaptive mutations. Genome Biol J. 10:R118.
Culver G.M., et al. (1999) Efficient reconstitution of functional *Escherichia coli* 30S ribosomal subunits from a complete set of recombinant small subunit ribosomal proteins. RNA J. 5:832-843.
Datta S., et al. (2006) A set of recombineering plasmids for gram-negative bacteria. Gene J. 379:109-115.
Davis J.H., et al. (2009) Engineering synthetic adaptors and substrates for controlled ClpXP degradation. Biol Chem J. 284:21848-21855.
de Sousa Abreu R., et al. (2009) Global signatures of protein and mRNA expression levels. Mol Biosyst J. 5:1512-1526.

(Continued)

*Primary Examiner* — Michele K Joike
*Assistant Examiner* — Mindy G Brown
(74) *Attorney, Agent, or Firm* — Akerman LLP

(57) ABSTRACT

The present application relates to methods, compositions and systems for the specific, controllable degradation of targeted proteins. Typically, the target proteins have a function which has not yet been elucidated. The disclosure enables one to study the effect of degrading a targeted protein, which in turn, will lead to a characterization of its function. In one embodiment, the invention pertains to a composition comprising a construct wherein the construct includes a peptide including a degradation tag. The degradation tag includes a ClpX binding sequence appended to a protein, wherein the sequence is YALAA.

19 Claims, 9 Drawing Sheets

(56) References Cited

PUBLICATIONS

Delvillani F., et al. (2011) S1 ribosomal protein and the interplay between translation and mRNA decay. Nucleic Acids Res. 39:7702-7715.

Draper D.E., et al. (1999) RNA binding strategies of ribosomal proteins. Nucleic Acids Res J. 27:381-388.

Farrell C.M., et al. (2005) Cytoplasmic degradation of ssrA tagged proteins. Mol Microbiol J. 57:1750-1761.

Feng Y., et al. (2001) *Escherichia coli* poly(A)-binding proteins that interact with components of degradosomes or impede RNA decay mediated by polynucleotide phosphorylase and RNase E. J Biol Chem J. 276:31651-31656.

Fleischmann R.D., et al. (1995) Whole-genome random sequencing and assembly of Haemophilus influenzae Rd. Science J. 269:496-512.

Flynn J.M., et al. (2001) Overlapping recognition determinants within the ssrA degradation tag allow modulation of proteolysis. Proc Natl Acad Sci U S A J. 98:10584-10589.

Fong S.S., et al. (2006) Latent pathway activation and increased pathway capacity enable *Escherichia coli* adaptation to loss of key metabolic enzymes. Biol Chem J. 281:8024-8033.

Fraser C.M., et al. (1995) The minimal gene complement of *Mycoplasma genitalium*. Science J. 270:397-403.

Gama-Castro S., et al. (2008) RegulonDB (version 6.0): gene regulation model of *Escherichia coli* K-12 beyond transcription, active (experimental) annotated promoters and Textpresso navigation. Nucleic Acids Res J. 36:D120-D124.

Gerdes S.Y., et al. (2003) Experimental determination and system level analysis of essential genes in *Escherichia coli* MG1655. Bacteriol J. 185:5673-5684.

Glass J.I., et al. (2006) Essential genes of a minimal bacterium. Proc Natl Acad Sci U S A J. 103:425-430.

Gorke B., et al. (2008) Carbon catabolite repression in bacteria: many ways to make the most out of nutrients. Nat Rev Microbiol J. 6:613-624.

Gottesman S., et al. (1998) The ClpXP and ClpAP proteases degrade proteins with carboxy-terminal peptide tails added by the SsrA-tagging system. Genes Dev J. 12:1338-1347.

Griffith K.L., et al. (2008) Inducible protein degradation in Bacillus subtilis using heterologous peptide tags and adaptor proteins to target substrates to the protease ClpXP. Mol Microbiol J. 70:1012-1025.

Handford J.I., et al. (2009) Conserved network of proteins essential for bacterial viability. Bacteriol J. 191:4732-4749.

Hayes C.S., et al. (2002) Proline residues at the C terminus of nascent chains induce SsrA tagging during translation termination. Biol Chem J. 277:33825-33832.

Held W.A., et al. (1973) Reconstitution of *Escherichia coli* 30 S ribosomal subunits from purified molecular components. Biol Chem J. 248:5720-5730.

Hemm M.R., et al. (2010) Small stress response proteins in *Escherichia coli*: proteins missed by classical proteomic studies. Bacteriol J. 192:46-58.

Herring C.D., et al. (2006) Comparative genome sequencing of *Escherichia coli* allows observation of bacterial evolution on a laboratory timescale. Nat Genet J. 38:1406-1412.

Herring C.D., et al. (2004) Conditional lethal amber mutations in essential *Escherichia coli* genes. Bacteriol J. 186:2673-2681.

Hobbs E.C., et al. (2010) Small RNAs and small proteins involved in resistance to cell envelope stress and acid shock in *Escherichia coli*: analysis of a bar-coded mutant collection. Bacteriol J. 192:59-67.

Hook-Barnard I.G., et al. (2007) Identification of an AU-rich translational enhancer within the *Escherichia coli* fepB leader RNA. Bacteriol J. 189:4028-4037.

Hutchison C.A., et al. (1999) Global transposon mutagenesis and a minimal Mycoplasma genome. Science J. 286:2165-2169.

Ideker T., et al. (2001) Integrated genomic and proteomic analyses of a systematically perturbed metabolic network. Science J. 292:929-934.

Ishii N., et al. (2006) Experimental and computational assessment of conditionally essential genes in *Escherichia coli*. Bacteriol J. 188:8259-8271.

Jacob F., et al. (1961) Genetic regulatory mechanisms in the synthesis of proteins. Mol Biol J. 3:318-356.

Jenks P.J., et al. (2001) Identification of nonessential *Helicobacter pylori* genes using random mutagenesis and loop amplification. Res Microbiol J. 152:725-734.

Jennings L.D., et al. (2008) ClpP hydrolyzes a protein substrate processively in the absence of the ClpA ATPase: mechanistic studies of ATPindependent proteolysis. Biochemistry J. 47:11536-11546.

Jones P.G., et al. (1996) Cold shock induces a major ribosomal-associated protein that unwinds double-stranded RNA in *Escherichia coli*. Proc Natl Acad Sci U S A J. 93:76-80.

Joyce A.R., et al. (2006) Experimental and computational assessment of conditionally essential genes in *Escherichia coli*. J Bacteriol. 188:8259-8271.

Kaberdina A.C., et al. (2009) An unexpected type of ribosomes induced by kasugamycin: a look into ancestral times of protein synthesis? Mol Cell J. 33:227-236.

Kalapos M.P., et al. (1997) Identification of ribosomal protein S1 as a poly(A) binding protein in *Escherichia coli*. Biochimie J. 79:493-502.

Karp P.D., et al. (1996) EcoCyc: an encyclopedia of *Escherichia coli* genes and metabolism. Nucleic Acids Res 2 J. 4:32-39.

Karzai A.W., et al. (1999) SmpB, a unique RNA-binding protein essential for the peptide-tagging activity of SsrA (tmRNA). EMBO J 18:3793-3799.

Keiler K.C., et al. (1996) Role of a peptide tagging system in degradation of proteins synthesized from damaged messenger RNA. Science J. 271:990-993.

Kenniston J.A., et al. (2005) Partitioning between unfolding and release of native domains during ClpXP degradation determines substrate selectivity and partial processing. Proc Natl Acad Sci U S A J. 102:1390-1395.

Kingston R.E., et al. (2001) Guanidine methods for total RNA preparation. Curr Protoc Mol Biol J. Chapter 4: Unit 4.2.

Kitakawa M., et al. (1982) An amber mutation in the gene rpsA for ribosomal protein S1 in *Escherichia coli*. Mol Gen Genet J. 185:445-447.

Kobayashi K., et al. (2003) Essential *Bacillus subtilis* genes. Proc Natl Acad Sci U S A J. 100:4678-4683.

Kunst F., et al. (1997) The complete genome sequence of the gram-positive bacterium *Bacillus subtilis*. Nature J. 390:249-256.

Kwon Y.M., et al. (2003) Isolation of Salmonella typhimurium Tn5 mutants defective for survival on egg shell surface using transposon footprinting. J Environ Sci Health B J. 38:103-109.

Lee C., et al. (2001) ATP-dependent proteases degrade their substrates by processively unraveling them from the degradation signal. Mol Cell J. 7:627-637.

Levchenko I., et al. (2000) A specificity-enhancing factor for the ClpXP degradation machine. Science J. 289:2354-2356.

Liberati N.T., et al. (2006) An ordered, nonredundant library of Pseudomonas aeruginosa strain PA14 transposon insertion mutants. Proc Natl Acad Sci U S A J. 103:2833-2838.

Lies M., et al. (2008) Turnover of endogenous SsrA-tagged proteins mediated by ATP-dependent proteases in *Escherichia coli*. Biol Chem J. 283:22918-22929.

Livny J., et al. (2007) Identification of small RNAs in diverse bacterial species. Curr Opin Microbiol J. 10:96-101.

Malys N., et al. (2011) Translation initiation: variations in the mechanism can be anticipated. Cell Mol Life Sci J. 68:991-1003.

Marchler-Bauer A., et al. (2009) CDD: specific functional annotation with the Conserved Domain Database. Nucleic Acids Res J. 37:D205-D210.

Martin A., et al. (2008) Diverse pore loops of the AAA+ ClpX machine mediate unassisted and adaptor-dependent recognition of ssrA-tagged substrates. Mol Cell J. 29:441-450.

Martin A., et al. (2008) Pore loops of the AAA+ ClpX machine grip substrates to drive translocation and unfolding. Nat Struct Mol Biol J. 15:1147-1151.

(56) References Cited

OTHER PUBLICATIONS

Martin A., et al. (2008) Protein unfolding by a AAA+ protease is dependent on ATP-hydrolysis rates and substrate energy landscapes. Nat Struct Mol Biol J. 15:139-145.

McGinness K.E., et al. (2006) Engineering controllable protein degradation. Mol Cell J. 22:701-707.

Mendoza-Vargas A., et al. (2009) Genome-wide identification of transcription start sites, promoters and transcription factor binding sites in *E. coli*. PLoS One 4:J. e7526.

Moll I., et al. (2002) Differential inhibition of 30S and 70S translation initiation complexes on leaderless mRNA by kasugamycin. Biochem Biophys Res Commun J. 297:1021-1026.

Moll I., et al. (2002a) Effects of ribosomal proteins S1, S2 and the DeaD/CsdA DEAD-box helicase on translation of leaderless and canonical mRNAs in *Escherichia coli*. Mol Microbiol J. 44:1387-1396.

Moll I., et al. (2002b) Leaderless mRNAs in bacteria: surprises in ribosomal recruitment and translational control. Mol Microbiol J. 43:239-246.

Monod J. (1949) The Growth of Bacterial Cultures. Annual Reviews of Microbiology J. 3:371-394.

Moore S.D., et al. (2001) Structural transformations accompanying the assembly of bacteriophage P22 portal protein rings in vitro. Biol Chem J. 276:6779-6788.

Moore S.D., et al. (2002) A P22 scaffold protein mutation increases the robustness of head assembly in the presence of excess portal protein. Virol J. 76:10245-10255.

Moore S.D. et al. (2002) Bacteriophage p22 portal vertex formation in vivo. Mol Biol J. 315:975-994.

Moore S.D., et al. (2005) Ribosome rescue: tmRNA tagging activity and capacity in *Escherichia coli*. Mol Microbiol J. 58:456-466.

Moore S.D., et al. (2007) The tmRNA system for translational surveillance and ribosome rescue. Annu Rev Biochem J. 76:101-124.

Moore S.D., et al. (2008) Revisiting the mechanism of macrolide-antibiotic resistance mediated by ribosomal protein L22. Proc Natl Acad Sci U S A J. 105:18261-18266.

Moore S.D., et al. (2008) Forced extraction of targeted components from complex macromolecular assemblies. Proc Natl Acad Sci U S A J. 105:11685-11690.

Moore S.D. (2011) Assembling new *Escherichia coli* strains by transduction using phage P1. Methods Mol Biol J. 765:155-169.

Mushegian A.R., et al. (1996) A minimal gene set for cellular life derived by comparison of complete bacterial genomes. Proc Natl Acad Sci U S A J. 93:10268-10273.

Nakagawa S., et al. (2010) Dynamic evolution of translation initiation mechanisms in prokaryotes. Proc Natl Acad Sci U S A J. 107:6382-6387.

Oehler S. (2009) Feedback regulation of Lac repressor expression in *Escherichia coli*. Bacteriol J. 191:5301-5303.

O'Farrell H.C., et al. (2008) Sequence and structural evolution of the KsgA/Dim1 methyltransferase family. BMC Res Notes J. 1:108.

Peil L., et al. (2008) Ribosome assembly in *Escherichia coli* strains lacking the RNA helicase DeaD/CsdA or DbpA. FEBS J 275:3772-3782.

Phadtare S., et al. (2010) RNA remodeling and gene regulation by cold shock proteins. RNA Biol J. 7:788-795.

Portier C., et al. (1984) Expression of the rpsO and pnp genes: structural analysis of a DNA fragment carrying their control regions. Nucleic Acids Res J. 12:6091-6102.

Pruss B.M., et al. (2010) Environmental and genetic factors that contribute to *Escherichia coli* K-12 biofilm formation. Arch Microbiol. 192:715-728.

Prud'homme-Genereux A., et al. (2004) Physical and functional interactions among RNase E, polynucleotide phosphorylase and the cold-shock protein, CsdA: evidence for a 'cold shock degradosome'. Mol Microbiol J. 54:1409-1421.

Py B., et al. (1996) A DEAD-box RNA helicase in the *Escherichia coli* RNA degradosome. Nature J. 381:169-172.

Raghavan R., et al. (2011) Genome-wide identification of transcription start sites yields a novel thermosensing RNA and new cyclic AMP receptor protein-regulated genes in *Escherichia coli*. Bacteriol J. 193:2871-2874.

Rasmussen M.D., et al. (1993) Isolation and characterization of mutants with impaired regulation of rpsA, the gene encoding ribosomal protein S1 of *Escherichia coli*. Mol Gen Genet J. 240:23-28.

Roche E.D., et al. (2001) Identification of endogenous SsrA-tagged proteins reveals tagging at positions corresponding to stop codons. Biol Chem J. 276:28509-28515.

Rudd K.E. (2000) EcoGene: a genome sequence database for *Escherichia coli* K-12. Nucleic Acids Res J. 28:60-64.

Ruijter J.M., et al. (2009) Amplification efficiency. linking baseline and bias in the analysis of quantitative PCR data. Nucleic Acids Res J. 37:e45.

Sassetti C.M., et al. (2001) Comprehensive identification of conditionally essential genes in mycobacteria. Proc Natl Acad Sci U S A J. 98:12712-12717.

Sassetti C.M., et al. (2003) Genes required for mycobacterial growth defined by high density mutagenesis. Mol Microbiol J. 48:77-84.

Sergiev P. V., et al. (2007) Ribosomal RNA guanine-(N2)-methyltransferases and their targets. Nucleic Acids Res J. 35:2295-2301.

Seta F. D., et al. (1997) Characterization of *Escherichia coli* strains with gapA and gapB genes deleted. J Bacteriol J. 179:5218-5221.

Shajani Z., et al. (2011) Assembly of bacterial ribosomes. Annu Rev Biochem J. 80:501-526.

Sharan S. K., et al. (2009) Recombineering: a homologous recombination-based method of genetic engineering. Nat Protoc J. 4:206-223.

Shin Y., et al. (2009) Single-molecule denaturation and degradation of proteins by the AAA+ ClpXP protease. Proc Natl Acad Sci U S A J. 106:19340-19345.

Shultzaberger R. K., et al. (2001) Anatomy of *Escherichia coli* ribosome binding sites. Mol Biol J. 313:215-228.

Skorski P., et al. (2006) The highly efficient translation initiation region from the *Escherichia coli* rpsA gene lacks a shine-dalgarno element. Bacteriol J. 188:6277-6285.

Skouv J., et al. (1990) Ribosomal protein S1 of *Escherichia coli* is the effector for the regulation of its own synthesis. Biol Chem J. 265:17044-17049.

Sorensen M.A., et al. (1998) Ribosomal protein S1 is required for translation of most, if not all, natural mRNAs in *Escherichia coli* in vivo. Mol Biol J. 280:561-569.

Sorokin A., et al. (1995) The *Bacillus subtilis* chromosome region encoding homologues of the *Escherichia coli* mssA and rpsA gene products. Microbiology J. 141 (Pt 2):311-319.

Stein L.D., et al. (2002) The generic genome browser: a building block for a model organism system database. Genome Res J. 12:1599-1610.

Studier F. W. (2005) Protein production by auto-induction in high density shaking cultures. Protein Expr Purif J. 41:207-234.

Suryanarayana T., et al. (1983) An essential function of ribosomal protein S1 in messenger ribonucleic acid translation. Biochemistry J. 22:2715-2719.

Szyk A., et al. (2006) Crystal structure at 1.9A of *E. coli* ClpP with a peptide covalently bound at the active site. Struct Biol J. 156:165-174.

Tatusov R. L., et al. (2000) The COG database: a tool for genome-scale analysis of protein functions and evolution. Nucleic Acids Res J. 28:33-36.

Tedin K., et al. (1997) Requirements for ribosomal protein S1 for translation initiation of mRNAs with and without a 5' leader sequence. Mol Microbiol J. 25:189-199.

Thouvenot B., et al. (2004) The strong efficiency of the *Escherichia coli* gapA P1 promoter depends on a complex combination of functional determinants. Biochem J. 383:371-382.

Tong X., et al. (2004) Genome-scale identification of conditionally essential genes in *E. coli* by DNA microarrays. Biochem Biophys Res Commun J. 322:347-354.

(56) References Cited

OTHER PUBLICATIONS

Toone W.M., et al. (1991) deaD, a new *Escherichia coli* gene encoding a presumed ATP-dependent RNA helicase, can suppress a mutation in rpsB, the gene encoding ribosomal protein S2. Bacteriol J. 173:3291-3302.

Traxler M.F., et al. (2008) The global, ppGpp-mediated stringent response to amino acid starvation in *Escherichia coli*. Mol Microbiol J. 68:1128-1148.

Uliczka F., et al. (2011) Monitoring of Gene Expression in Bacteria during Infections Using an Adaptable Set of Bioluminescent, Fluorescent and Colorigenic Fusion Vectors. PLoS One 6: J. e20425.

Van Melderen L., et al. (2009) Regulation and quality control by Lon-dependent proteolysis. Res Microbiol J. 160:645-651.

Vemuri G.N., et al. (2005) Metabolic engineering in the—omics era: elucidating and modulating regulatory networks. Microbiol Mol Biol Rev J. 69:197-216.

Vesper O., et al. (2011) Selective translation of leaderless mRNAs by specialized ribosomes generated by MazF in *Escherichia coli*. Cell J. 147:147-157.

Wang J., et al. (1997) The structure of ClpP at 2.3 A resolution suggests a model for ATP-dependent proteolysis. Cell J. 91:447-456.

Wong S.M., et al. (2000) Genetic footprinting with mariner-based transposition in *Pseudomonas aeruginosa*. Proc Natl Acad Sci U S A J. 97:10191-10196.

Xu L., et al. (2011) Altered nucleic acid partitioning during phenol extraction or silica adsorption by guanidinium and potassium salts. Anal Biochem. 419:309-316.

Yamaguchi Y., et al. (2009) mRNA interferases, sequence-specific endoribonucleases from the toxin-antitoxin systems. Prog Mol Biol Transl Sci J. 85:467-500.

Yamazaki Y., et al. (2008) Profiling of *Escherichia coli* Chromosome database. Methods Mol Biol J. 416:385-389.

Yoder-Himes, et al. (2009) Mapping the Burkholderia cenocepacia niche response via high-throughput sequencing. Proc Natl Acad Sci U S A J. 106:3976-3981.

Zolkiewski M. (2006) A camel passes through the eye of a needle: protein unfolding activity of Clp ATPases. Mol Microbiol J. 61:1094-1100.

Zuker M. (2003) Mfold web server for nucleic acid folding and hybridization prediction. Nucleic Acids Res J. 31:3406-3415.

Griffith, K.L. et al., Inducible protein degradation in *Bacillus subtilis* using heterologous peptide tags and adaptor proteins to target substrates to the protease ClpXP, Mol Microbiol, 2008, vol. 70, pp. 1012-1025.

Keiler, K.C. et al., Role of a peptide tagging system in degradation of proteins synthesized from damaged messenger RNA, Science, 1996, vol. 271, pp. 990-993.

McGinnis, K.E., et al., Engineering controllable protein degradation, Mol. Cell, 2006, vol. 22, pp. 701-707.

Moore, S.D. et al., Forced extraction of targeted components from complex macromolecular assemblies, Proc Natl Acad Sci USA, 2008, vol. 105, pp. 11685-11690.

Bollen A, et al. (1979) A conditionally lethal mutation of *Escherichia coli* affecting the gene coding for ribosomal protein S2 (rpsB). J Mol Biol. 132:219-233.

Farwell M, et al. (1992) The effect of ribosomal protein S1 from *Escherichia coli* and *Micrococcus luteus* on protein synthesis in vitro by *E. coli* and *Bacillus subtilis*. Mol Microbiol. 6(22):3375-3383.

Hoskins J, et al. (2002) Clp ATPases and their role in protein unfolding and degradation. Adv Protein Chem. 59:413-429.

Régnier P, et al. (1991) Decay of mRNA encoding ribosomal protein S15 of *Escherichia coli* is initiated by an RNase E-dependent endonucleolytic cleavage that removes the 3' stabilizing stem and loop structure. J Mol Biol. 217:283-292.

Subramanian AR. (1983) Structure and functions of ribosomal protein S1. Progress in Nucl Acid Res and Mol Biol. 28:101-142.

\* cited by examiner

Figure 6. Degradation of a Control Substrate
A GFP fusion with aminoglycoside acetyltransferase (AAC) was mixed with ClpX, ClpP, ATP and an ATP regeneration system and incubated at 30 °C. Samples were removed and analyzed by SDS PAGE and Coomassie staining. By 80 minutes, all of the substrate (10-fold over $ClpX_6$) was degraded.

CELLULAR DEPLETION OF BIOMOLECULAR TARGETS

CROSS-REFERENCE TO RELATED PATENT APPLICATION

This application claims the benefit of priority of U.S. patent application Ser. No. 61/445,648 filed 23 Feb. 2011, which is herein incorporated by reference in its entirety.

REFERENCE TO SEQUENCE LISTING

The Sequence Listing submitted Nov. 20, 2013 as a text file named "26150_0041 U2 Sequence_Listing.txt," created on Nov. 20, 2013, and having a size of 1,507 bytes is hereby incorporated by reference pursuant to 37 C.F.R. §1.52(e)(5).

FIELD OF THE INVENTION

This invention relates generally to a composition and methods for degrading target proteins in a cell as methods for the identification of the roles and functions of proteins in a cell.

BACKGROUND

The interface between genetics and biochemistry sits at the level of translation wherein mRNAs are selected from a large pool of competing transcripts and fed into ribosomes for protein synthesis. Choosing which mRNAs enter a translation system out of the thousands of competing substrates is a highly-orchestrated process that requires the activities of factors that recognize sequence determinants in messages during translation initiation (Malys and McCarthy, 2011). Aside from the transcriptional regulation that synthesizes the RNA pool, important complementary control systems rapidly sculpt transcriptomes by promoting RNA turnover (Arraiano et al., 2010; Burger et al., 2011). Thus, transcribed genetic information flows from the genome and partitions either into a decoding event or into a decay event. Once a message has been translated, a partitioning decision is again made, so the entire proteome is a reflection of a single molecular event that decides the fate of mRNAs.

Of the ~4,400 *Escherichia coli* (*E. coli*) open reading frames, roughly a third have not had their encoded protein functions experimentally verified (1-6). This collection of genes creates a significant black box in our understanding of fundamental cellular physiology, especially when considering those genes of unknown function that are essential for viability.

Much of what is known about gene function has followed from studies in bacteria where there are suites of powerful tools available that have been refined in model systems such as *E. coli*. Despite astounding advances in DNA sequencing and synthesis technologies, there is a remaining fundamental question that has piqued the interest of hundreds of investigators: what are the minimal requirements for life? The predominant approaches to answering this question have been to either computationally compare genomes and identify conserved core genes or to randomly disrupt the genomes using transposons and deduce which genes do not tolerate interruption this is often referred to as "genetic footprinting" (1,2,14-16). These combined strategies form the cornerstone of our understanding of what comprises an essential genome.

Numerous bacterial genera have had their genomes interrogated both computationally and experimentally in an effort to reveal what the most important features are in a genome. These include early comparisons of *Mycoplasma* and *Haemophilus* (14-18), followed by *Bacillus* (19,20), *Mycobacterium* (21,22), *Pseudomonas* (23,24), *Helicobacter* (25), *Salmonella* (26), and *Escherichia* (1,2,27). Using genetic tools to directly test the importance of protein-encoding genes, Baba et al. determined that approximately 300 ORFs appear to be essential for *E. coli* growth (1). The recent additions of open reading frames that were not annotated at the time the footprinting and recombineering studies were performed may be among the most dramatic changes to the list of *E. coli* genes. Many of these ORFs (~60) are very small (<50 amino acids) yet clearly play a role in cellular physiology (3,4) Likewise, other genes (~100) that encode small RNAs and appear to be important are also new additions (4,28,29). Thus, even the assignment of how many genes *E. coli* has is changing on a regular basis.

In bacteria, orthologs of the ribosomal protein S1 are the gatekeepers that shuttle mRNA into the translation pool by promoting associations with the small subunit during translation initiation. Of these, the S1 protein of *Escherichia coli* is the best characterized (Delvillani et al., 2011; Feng et al., 2001; Moll et al., 2002a; Nakagawa et al., 2010; Subramanian, 1983; Suryanarayana and Subramanian, 1983). Despite being the largest ribosomal protein in *E. coli*, it is a weakly-associated factor that may cycle on and off ribosomes during the translation cycle (Culver and Noller, 1999; Held et al., 1973; Subramanian, 1983). S1 is comprised of multiple RNA binding domains and tethers mRNAs to the small subunit via an interaction that requires the presence of ribosomal protein S2 (Boileau et al., 1981; Bollen et al., 1979; Moll et al., 2002a). An added feature of *E. coli's* S1 is that it also directly interacts with RNase E and PNPase, each components of the degradosome, which is responsible for bulk RNA turnover (Arraiano et al., 2010; Burger et al., 2011; Feng et al., 2001; Prud'homme-Généreux et al., 2004; Py et al., 1996).

DETAILED DESCRIPTION

Figure 1:
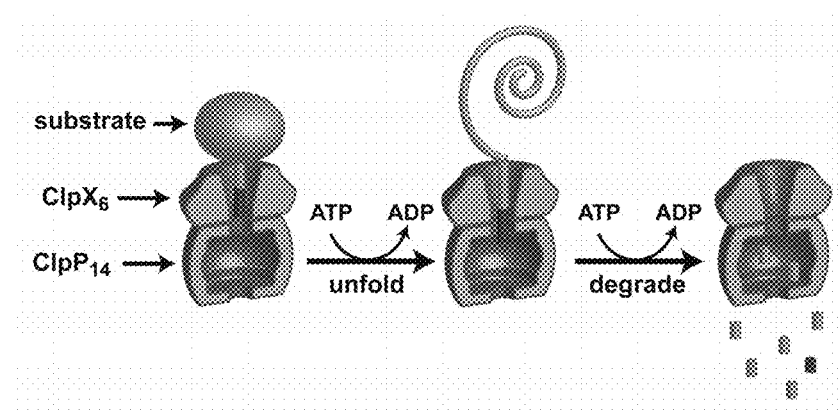
FIG. 1. ClpXP unfolds and degrades protein substrates. Proteins bearing a degradation peptide (red) are recognized by ClpX (blue), unfolded and processively translocated through the pore of ClpP (green) where degradation occurs. ATP hydrolysis provides the unfolding and translocation energy.

Embodiments of the invention enable the conditional, specific and rapid depletion of a specific protein from cells, cell extracts, or purified systems. In certain embodiments, target proteins are fused to an engineered peptide tag that allows for recognition and degradation by a processive protease. Degradation can be induced by activating the proteolytic activity, either by induction of the protease, induction of an adapter for the protease, or by addition of the protease to mixtures. Prior to target depletion, cells are maintained in a healthy state with normal levels of the target protein. Therefore, selective pressures that may give rise to secondary mutations or re-balancing of cellular physiology are avoided. Target proteins undergoing degradation are substantially removed so residual or alternate activities that can be present in conditional mutants do not interfere. The technology allows for the creation of novel cell physiologies. Cells lacking a putative drug target can be generated for comparative studies or for control experiments. Additionally, cell extracts or macromolecular assemblies can be generated that lack a specific component even if that component is necessary for the formation of the original complex.

Embodiments of the invention avoid any requirement of depletion of a protein of study after down-regulation of the target expression. This type of depletion requires either multiple rounds of cell division or a long incubation time for natural turnover to deplete the protein. Such delays mask the immediate cellular responses to depletion. Also, if the target protein is required for cell division, depletion may not be possible. Embodiments of the invention do not require knowledge of the function of the protein for isolating conditional mutants (cold-ortemperature-sensitive for example). To the inventor's knowledge, the present application includes the first teaching of systems and methods that enable a direct assessment of the importance of the encoded gene product, not simply the gene sequence.

Prior art that employs genetic strategies to deplete protein activity require the maintenance and growth of cells under conditions that can give rise to second-site mutations that mask growth and physiology defects associated with the damaged gene. Conditional mutants of target proteins generally only inactivate one feature of a protein and any other interactions of the target protein are not removed. Therefore, proteins with multiple enzymatic activities or binding interfaces are not completely inactivated.

The pool of mRNA in a cell is shaped by both the synthesis and degradation rates of each particular transcript. Engagement with ribosomes generally serves to protect mRNAs and extend their lifetimes, so the mechanisms that govern access to the translation machinery are critical to the expression of an appropriate proteome from a given transcriptome. Whether S1 is directly or indirectly responsible for regulating transcript levels remains heretofore unclear. However, a novel system has been developed herein, in an embodiment, to allow for the rapid depletion of S1 using targeted protein degradation that does not require cell division or extended incubations so that the direct influences of S1 on transcript levels can be assessed. Measurements of the changes in mRNA levels on selected genes during S1 depletion, as demonstrated herein, demonstrate that S1 generally acts to stabilize messages. However, some messages were found unaffected by S1 depletion and the gapA and csdA mRNAs were particularly sensitive to the presence of S1. Therefore, it has been discovered herein, that S1 is not simply a general translation initiation factor that recruits mRNAs as a function of affinity and abundance, rather, it serves as a master regulator that is capable of directly influencing the transcriptome.

S1 was long thought to be absent in *Bacillus subtilis* and related bacteria because it is smaller and its presence was only recently revealed by genome sequence analysis (Farwell et al., 1992; Sørensen et al., 1998; Sorokin et al., 1995). The perceived absence of S1 in *B. subtilis* led to early conclusions that S1-deficient ribosomes preferentially recognized mRNAs with consensus Shine-Dalgarno sequences, but considering the presence of an S1 ortholog, and that S1 depletion restricts most translation, S1 apparently acts globally (Farwell et al., 1992; Sørensen et al., 1998). Interestingly, RNase E is absent in *B. subtilis* and so the difference in the character of S1 may be a reflection of a need to interact with alternative degradation factors (Arraiano et al., 2010). In all cases, it is important to consider that weaker interactions between the RNA degradation machinery and ribosomes are probably significantly disrupted in cell-free systems and, as a consequence, RNA and protein distributions in gradients and cell-free translation systems are not necessarily reflective of the intracellular environment.

S1 is essential, a property that has hampered detailed studies of its function in vivo (Briani et al., 2008; Kitakawa and Isono, 1982; Sørensen et al., 1998). However, a significant body of work has been published on the activity of S1-deficient ribosomes in vitro, which are prepared by passing ribosomes through poly-uridine columns in high salt. The use of S1-depleted ribosomes helps define the process by which ribosomes engage so called "leaderless" transcripts (lacking a 5'-UTR), providing that this form of translation initiation occurs through a direct partnering of 70S particles with these mRNAs without the help of S1 (Brock et al., 2008; Kaberdina et al., 2009; Moll and Bläsi, 2002; Moll et al., 2002b; Moll et al., 2002a; Tedin et al., 1997). The design and expression of numerous model reporter transcripts with assorted 5' UTRs reinforces our current understanding of S1 as a regulator of translation initiation (Briani et al., 2008; Delvillani et al., 2011; Draper and Reynaldo, 1999; Moll et al., 2002a; Subramanian, 1983).

It has been discovered herein, that eliminating S1 in living cells allows for comparative studies to be performed in a natural setting. For example, such systems permit measurements of mRNA abundance and turnover as well as a determination of the influence of S1 on selective translation initiation. Toward this goal, two groups have placed rpsA under a controllable promoter so that S1 expression could be conditionally down-regulated (Briani et al., 2008; Sørensen et al., 1998). These studies confirmed that S1 expression is essential for growth. In one case, the effect of S1 depletion on protein synthesis was monitored and it was observed that there was a global reduction in protein synthesis with the expression of translation factors being preferred at later timepoints (Sørensen et al., 1998). This observation suggests that S1 may be required for nearly all canonical translation initiation events. However, the relative abundances of mRNAs encoding the persistently-translated proteins upon S1 depletion were not determined and changes to the transcriptome may have influenced the observed translation biases. In support of this notion, other studies revealed that prolonged depletion of S1 caused a significant reduction in the abundance of many mRNAs, including some of those encoding factors responsible for RNA turnover (Briani et al., 2008; Delvillani et al., 2011). Thus, the inventors have identified that S1 appears to also regulate the synthesis of RNA-turnover machinery, in addition to its role in mRNA partitioning.

As with many "depletion-by-cell-division" experiments involving essential factors, turning off the expression of S1 led to a reduction in growth rate and several hours were required for a reduction in S1 sufficient to stop cell-division (Briani et al., 2008; Sørensen et al., 1998). This scenario raises the possibility that secondary events may have played a role in the observed changes in physiology that are indirectly related to S1 depletion. One consideration is the possible activation of toxin components when their less-stable antitoxin partners were no longer efficiently produced (Condon, 2006; Vesper et al., 2011; Yamaguchi and Inouye, 2009). In order to overcome these limitations, gene product abundance is targeted, instead of gene expression, for conditional reduction. Recent advances in the understanding of directed proteolysis now permit targeted protein depletion as a viable strategy (Baker and Sauer, 2011; Griffith and Grossman, 2008; McGinness et al., 2006).

In one embodiment, a targeted degradation system to rapidly deplete S1 from *E. coli* has been developed herein in order to provide the ability to observe physiological changes closely related to the direct function of S1. As described and demonstrated herein, in a non-limiting embodiment, this system was able to reduce S1 to trace levels in less than 25 minutes without the need for cell division. As a preliminary analysis of the consequence of rapid S1 depletion, the amounts of several mRNAs that were either related or unrelated to S1 function were monitored to gain a clearer picture of the influence this factor has on regulating mRNA abundance as well as to use as a comparison with traditional S1 depletion studies. For most of the monitored mRNAs, a significant influence of S1 on message abundance was observed, which was consistent with the role of S1 as a general stabilizing factor. In contrast, it was discovered herein that the levels of some mRNAs were unaffected by the presence of S1 while others were drastically altered. These findings demonstrate that certain messages are particularly sensitive to S1 regulation. Among these, pronounced and differential changes to the levels of gapA and csdA transcripts provide a link between ribosome activity and central metabolic processes.

Reference will be made below in detail to exemplary embodiments of the invention; however the invention is not limited to those embodiments described below. The particular examples are provided to aid in fully describing the embodiments presented, and are not to be construed as limiting the invention to those particular embodiments or examples. *E. coli* is used below in various examples; however it is only provided as an example and is not intended to be limiting of the application of the invention.

As alluded to above, the present application relates generally to the identification and the study of the function of genes whose function is unknown. In order to study these functions, in a non-limiting embodiment, the invention pertains to introducing a tag into a cell, wherein the tag includes a sequence which is recognized by a protease. Optionally, the protease can be introduced into the cell as well, which then targets the tagged sequence resulting in degradation of the tagged sequence and in turn degrading any protein onto which said tagged sequence is attached. The characteristics of the cell in response to the degradation of the particular sequence can be studied in order to determine the previously unknown function of the particular gene encoding the protein having the tagged sequence. Moreover, the present application relates to methods, compositions and systems for the specific degradation of targeted proteins. Typically, the target proteins have a function which may not yet have been elucidated. The disclosure enables one to study the effect of degrading a targeted protein, which in turn, will lead to a characterization of its function.

In a further embodiment, the invention pertains to a composition comprising a vector wherein the vector includes a peptide including a degradation tag. The degradation tag typically includes a ClpX binding sequence appended to a protein. In a specific embodiment, the ClpX binding sequence is YALAA. In another embodiment there is provided a method for determining the role of a protein of unknown function in a cell. The method includes degrading a target protein of unknown function in a cell. The degrading includes engineering the cell to comprise a degradation tag, wherein the tag includes a ClpX binding sequence, and wherein the sequence is YALAA, further introducing a protease specific to the binding sequence into the cell, and monitoring the cell for physiological changes.

In further embodiment, the invention provides a method of degrading a target protein in a cell, including inserting a tag sequence into a target site of the cell chromosome, wherein the tag sequence is YALAA. The tag sequence further including a degradation tag, a drug marker, and a 5' flanking region and a 3' flanking region. The 5' and 3' flanking regions include a recognition sequence corresponding to the target site, such that the tag sequence is introduced at the end of the target site by recombination, wherein transcription and translation result in a protein containing the degradation tag and the drug marker. The method further provides introducing a protease complex, wherein the complex recognizes and associates with the tag sequence and upon activation of the protease complex the target protein is degraded.

An additional manner of discovering the function of proteins of unknown function have been discovered. In an additional embodiment, there is provided a method of identifying the function of protein-coding genes, including: performing controlled degradation of cells with target proteins of known function, performing controlled degradation of cells with proteins of unknown function, characterizing and analyzing physiological changes in cells missing proteins of known function, characterizing and analyzing physiological changes in cells missing proteins of unknown function; and then evaluating the differences between the two types of cells in order to determine the function of the proteins of unknown function.

By studying essential gene function, physiological responses that accompany the depletion of an essential protein can be used to reveal the pathways which are most influenced by the protein's normal function. This is supported by the well-established concept that genes of related function are generally co-regulated. Support is also provided by the numerous studies that reveal changes in the transcription profiles of related genes upon inactivation or depletion of certain important proteins (7-13).

By way of background, it is noted that *E. coli* have a collection of energy-dependent proteases that couple ATP hydrolysis to the translocation of a substrate protein to a sequestered proteolytic chamber. These include ClpXP, ClpAP, lon, HslUV, and FtsH (39-43). The best characterized of these proteases is ClpXP, a complex of a hexamer of the ClpX unfoldase and the 14-mer ClpP protease (43-47). Upon substrate recognition, ClpX uses the energy from ATP hydrolysis to processively translocate along the substrate polypeptide chain, unfolding the substrate, and delivering the unfolded protein into the lumen of the ClpP structure where it encounters a high concentration of serine protease active sites (48,49). In FIG. 1, the substrate is completely degraded to small peptides (50). Proteins in FIG. 1 bearing a degradation peptide (red) are recognized by ClpX (blue), and are unfolded and processively translocated through the pore of ClpP (green) where degradation occurs. ATP hydrolysis provides the unfolding and translocation energy for this process.

ClpXP is the principle protease responsible for the degradation of proteins tagged by the tmRNA quality control system (encoded by the smpB and ssrA genes in *E. coli*) (51-54). Ribosome stalling during translation allows tmRNA to enter the ribosome and switch translation from the mRNA to a small ORF in tmRNA that encodes the "ssrA tag" which is a potent ClpX recognition signal (53,55). Thus, the released ssrA-tagged proteins are rapidly degraded by ClpXP. Importantly, prior work by the inventors revealed that there are hundreds of ribosome-rescue events per cell generation resulting in hundreds of different proteins tagged by tmRNA and degraded by ClpXP (56,57). Thus, ClpXP has evolved to degrade a wide variety of protein substrates.

Figure 2:
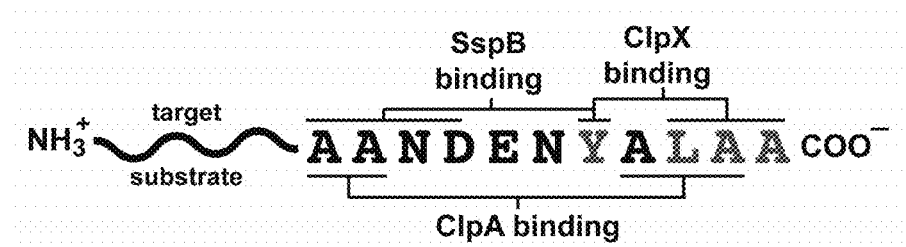
FIG. 2. The ssrA Degradation Tag. The eleven amino acid degradation tag (SEQ ID NO:1) added during ribosome rescue by tmRNA in *E. coli* is shown appended to a target substrate. Amino acids that reduce ClpX binding by 2-fold or more are shown in red. Residues required for efficient recognition by the adapter protein SspB and the unfoldase ClpA are also indicated. Note that the SspB and ClpA binding sites can be interrupted without interfering with ClpX recognition (58-60).

Substrate binding and degradation studies have identified the amino acid residues of the ssrA tag that are responsible for ClpX recognition (53, 58-60). In addition to these residues, the amino acids needed for ClpAP recognition (another protease that can degrade ssrA-tagged proteins) have been defined as well as those needed for binding by the protein SspB, a substrate adapter that helps deliver ssrA-tagged proteins to ClpXP (FIG. 2) (54,58-61). A method for conditionally-controlling the degradation of a target by re-engineering the ssrA tag such that it was only recognized by ClpXP in the presence of the SspB adapter has been developed (60, 63). Typically, proteins targeted by these strategies are degraded to undetectable levels in 15-30 minutes upon induction of the degradation system (60, 64). Moreover, the intrinsic degradation capability for endogenous levels of ClpXP to degrade ssrA-tagged substrates exceeds 100,000 per cell in 30 minutes (65). Thus, the ClpXP protease is a powerful, specific and efficient enzyme well-suited for the degradation of ssrA-bearing substrates.

Figure 3:
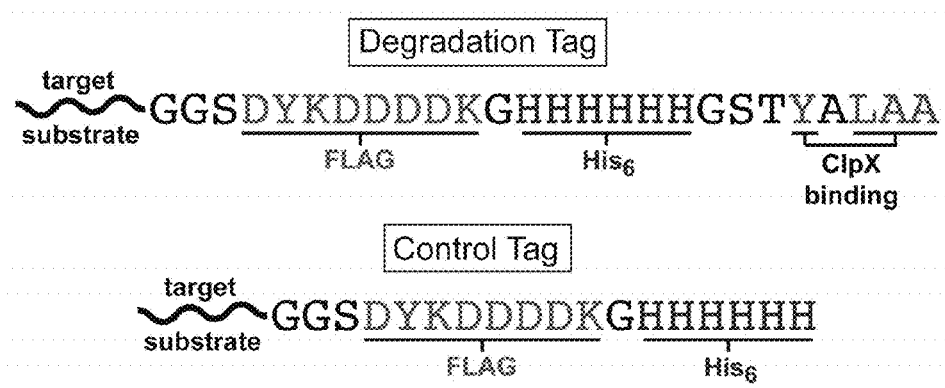
FIG. 3. A Re-Engineered Degradation Tag. When appended to a protein, the degradation tag (SEQ ID NO:2) allows for detection and purification using the FLAG and His6 epitopes and the ClpX binding sequence allows for degradation in the presence of ClpX. The DNA encoding the paired control tag (SEQ ID NO:3) has a stop codon after the His6 coding sequence and generates a shorter, stable peptide.

To this effect, one embodiment comprises a composition including a vector wherein the vector includes a peptide comprising a degradation tag. The tag includes a ClpX binding sequence appended to a protein, wherein the sequence is YALAA. In prior studies, significant effort was focused on subcloning and engineering for a single target at a time. Prior studies were focused on refining this strategy such that a large number of proteins could be targeted for conditional degradation with relative ease. However, the degradation tags used in prior studies were not suitable for a general targeting system. In short, a full-length ssrA tag recruits ClpAP leading to undesirable degradation and SspB binding leads to inappropriate dimerization of the target in the cell. While the prior studies could be performed in clpA-cells, it was determined that having active ClpAP would help to reduce the competing background of endogenous ssrA-tagged proteins (51,54,59). When the adapter-dependent tags were appended to target proteins, a variable level of background degradation was observed, depending on the target protein. Presumably, ClpXP (or another protease) exhibited differing affinities for the target in the absence of the adapter as has been reported in *Bacillus* (63). Based on this realization, it would be beneficial to use a degradation tag that contains a complete ClpX recognition determinant and that lacks determinants necessary for ClpA and SspB binding (FIG. 3). In a particular embodiment, the composition is provided wherein the tag sequence does not bind to ClpA or SspB. In a further embodiment, the composition of the subject invention is provided, wherein the tag sequence lacks a binding sequence for ClpA and SspB.

The current degradation tag may additionally contain flexible linker sequences to project the ClpX recognition signal away from the target (full ClpX engagement requires the tag to enter deep into the pore of the ClpX hexamer) (46). Accordingly, in another embodiment, the composition is provided wherein the degradation tag includes a FLAG tag. In a further embodiment, the degradation tag includes an $His_6$ epitope. These two different epitope tags were included to serve multiple functions. The $His_6$ tag can be used in one example for metal-affinity purification of a native target as well as detection with antibodies. Likewise, a FLAG tag is a useful epitope for immuno-detection and purification among other functions. An additional feature of the positioning of the FLAG tag is that the degradation of the target can be monitored with reasonable confidence that ClpX unfolded and degraded the target. This is possible because the distance from the pore of ClpX to the proteolytic sites in ClpP is ~40 amino acids in length so degradation of the FLAG epitope means that the FLAG sequence and at least 40 residues upstream have been translocated through the ClpX pore (45,62,66,67). A control tag that is added to each target in parallel has a stop codon inserted after the $His_6$ tag and does not encode a ClpX recognition signal (FIG. 3).

Furthermore, in another embodiment, the subject invention provides a method for determining the role of a protein of unknown function in a cell. The method includes degrading a target protein of unknown function in a cell. The degrading step includes engineering the cell to include a degradation tag, wherein the tag comprises a ClpX binding sequence, and the sequence is YALAA. The method further includes introducing a protease specific to the binding sequence into the cell, and monitoring the cell for physiological changes.

The method is provided where in one particular example, the cell is a bacterial cell. The method is provided in another example wherein the protease introduced into the cell is ClpXP. However, the method is not restricted to use in a bacterial cell and can be adapted for use in prokaryotic and eukaryotic cells. For example, other types of cells that could be used in accordance with the teachings herein include, but are not limited to, bacteria, yeast or mammalian cells, whether pathogenic or not. Also, a clinically important cell line could be used, wherein the system is designed to degrade a target protein for which researchers are attempting to design inhibitors. Researchers would be able to (1) see what the effect of full inhibition of the target would look like (by degrading the target), and (2) validate that their drug of interest is only inhibiting the intended target (by showing that there are no other effects of the drug when the target has been degraded).

In another embodiment, the method is provided wherein the ClpX binding sequence does not bind to ClpA or SspB. In a further embodiment, the sequence lacks a binding sequence for ClpA and SspB. In another embodiment, the method is provided, wherein the degradation tag comprises a FLAG tag. In yet a further embodiment, the method is provided, wherein the degradation tag comprises a $His_6$ epitope.

In another embodiment, the method is provided wherein a target protein of known function in a cell is degraded and monitored for physiological changes, and the physiological changes of the protein of known function are compared with the physiological changes of the target protein of unknown function. Exemplary physiological changes include growth, morphology, viability, gene expression patterns, and change in metabolite production.

In yet another embodiment, the method for determining the role of a protein of unknown function in a cell is provided, wherein a computationally predicted function of the protein of unknown function is obtained, and the physiological changes of the target protein of unknown function are compared with the computationally predicted function of the protein of unknown function. In a particular embodiment, the target protein is an essential protein. In an alternative embodiment, the target protein is nonessential.

Figure 4:
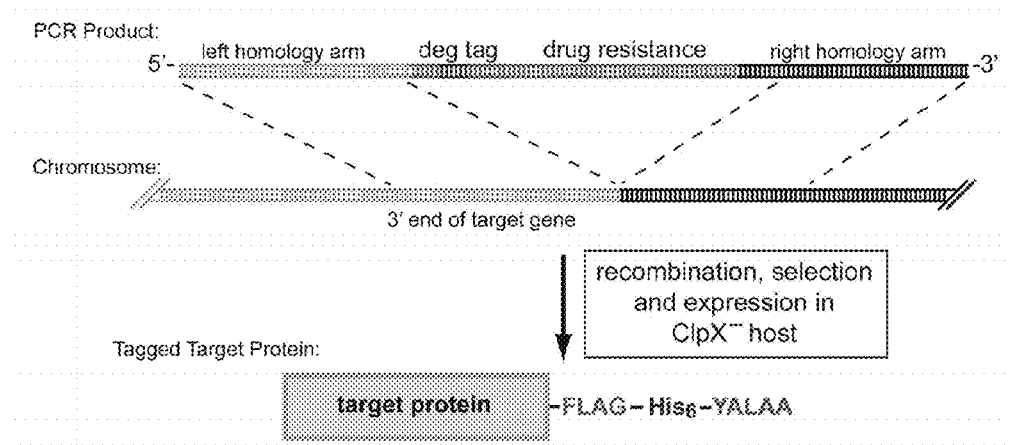
FIG. 4. Directed Recombination Adds the Degradation Tag Coding Sequence. Recombineering strategy used to append either the degradation or control tags to the ORFs of target genes. A PCR product containing the tag sequence and an antibiotic resistance marker is amplified to contain 50-bp homology arms that direct recombination to the end of the target gene. Once fused, all of the target protein that is expressed contains the appended tag (SEQ ID NO:4) making it a substrate for ClpXP. In the absence of ClpX, essential proteins can bear the degradation tag.

FIG. 4 demonstrates the recombination strategy used to append either the degradation or control tags to the ORFs of target genes. A PCR product containing the tag sequence and an antibiotic resistance marker is amplified to contain 50-bp homology arms that direct recombination to the end of the target gene. Once fused, the target protein that is expressed contains the appended tag making it a substrate for ClpXP. In the absence of ClpX, essential proteins can bear the degradation tag.

The tag-encoding sequence is positioned to the end of target genes by selecting for the adjacent antibiotic resistance marker (FIG. 4). One of three different markers (kanR, tetR, ampR) either coupled or uncoupled to the translation of a downstream ORF have been successfully used to add degradation tags to more than 13 proteins in ClpX– cells. The kanamycin resistance construct does not contain a promoter, and drug resistance is therefore dependent on transcription from the promoter of the target gene. Both the promoter-less kanR and the promoter containing tetR targeting constructs have been utilized in parallel and have not yet encountered difficulties arising from the tet promoter.

Successful recombinants were identified by colony formation on selective plates and subsequently screened using diagnostic PCR reactions. The integration region of the degradation tag and drug marker was then sequenced to verify the correct insertion and coding of the desired tag. In each case, to reduce the possibility of chromosomal rearrangements, the degradation tag sequence along with the drug resistance marker was transduced to a naïve strain and re-verified prior to making stocks.

Transducing lysates were used to attempt to move each marker into ClpX+ cells. Failure of ClpX+ cells to form transductants when a target protein contained the degradation tag provided direct evidence that the target protein was essential and that ClpX was capable of degrading the target. For example, when tagged versions of the essential frr or yeaZ genes (encoding ribosome recycling factor and a protein of unknown function respectively) were transduced into ClpX− cells, over a hundred colonies formed whereas none (or very few) colonies arose from cells that were ClpX+. Transductions that moved the control-tagged version of each gene gave similar colonies in both cases (Table 1). In contrast, transduction of selD (encoding selenophosphate synthase) with or without an encoded degradation signal yields similar numbers of colonies despite the fact that this gene was listed as essential in a report by Gerdes et al. Subsequent studies revealed that that selD may not be essential in E. coli (1,2). Using the teachings described herein, this has now been unequivocally confirmed by showing selD degradation by ClpX does not prevent growth.

To confirm the essentiality of the protein products of the frr and yeaZ genes and the non-essentiality of SelD, a plasmid containing the ClpX ORF was introduced under control of an arabinose-inducible promoter into otherwise ClpX− cells harboring these tagged genes. As controls, a mock plasmid that does not encode ClpX was used and the control strains bearing epitope tags lacking a ClpX recognition sequence. Plating of these cells on glucose-containing medium allowed for healthy growth in all cases whereas the frr-deg and yeaZ-deg strains failed to grow on plates with arabinose while their control counterparts lacking the ClpX recognition sequence grew well.

Figure 5:
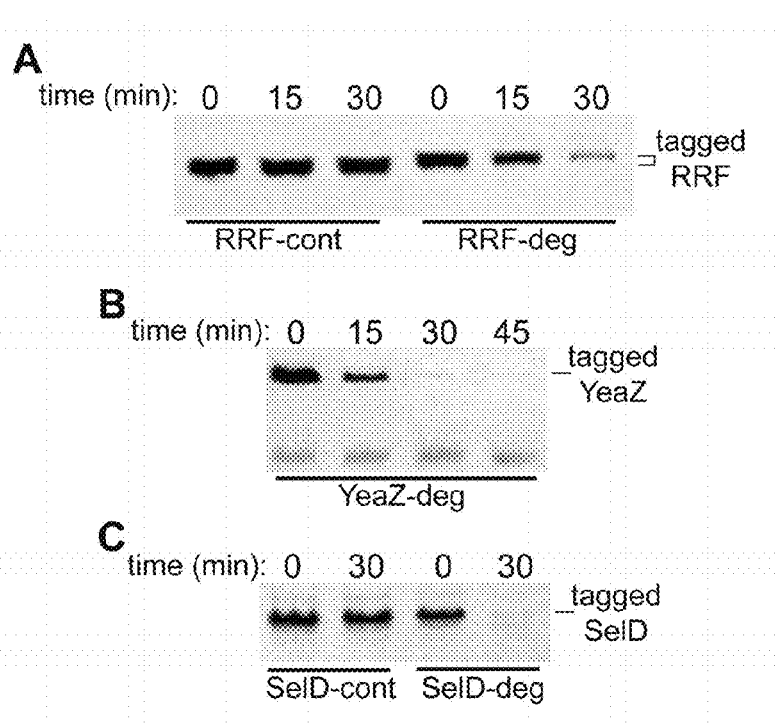
FIG. 5. ClpX ExpressionCauses Degradation of Target Proteins. Proteins bearing either a control (-cont) or a degradation (-deg) peptide were monitored in liquid cultures grown at 37 degrees Celsius by immunoblotting with anti-FLAG antibodies at selected times after the induction of ClpX from an arabinose-inducible plasmid. Panel A, degradation of RRF (encoded by frr). Panel B, degradation of Yeaz (no control-tagged version was included in this experiment). Panel C degradation of SelD. Loss of the FLAG epitope indicates a substantial portion of the target protein must have been unfolded and degraded.

To confirm that ClpX expression leads to the degradation of these targets, cultures of each strain were grown in a rich, defined medium and arabinose was used to induce ClpX expression while the cells were in log phase. At selected timepoints after ClpX induction, samples of the cultures were taken and the amount of target protein in normalized total cell lysates was determined using immuno-blots directed against the FLAG epitope (FIG. 5). In each case, the induction of ClpX led to a rapid reduction in target protein levels and after 30 minutes only small amounts could be detected. Since there was no inhibition of target protein expression in these experiments, the residual detectable level may reflect a small pool of protein that recently exited the ribosomes but had not yet been engaged by ClpXP. Nonetheless, induction of ClpX caused a cessation of growth of the frr-deg and yeaZ-deg strains and the protein targets were lowered to levels that would have taken more than four cell divisions in conventional gene depletion experiments. Additionally, it was determined that degradation of the target is not dependent on cell division; therefore a target protein that is directly involved in cell division can also be depleted.

TABLE 1

Testing Protein Essentiality with Transduction

| Gene | Encoded protein | Tag appended | ClpX− Transductants | ClpX+ Transductants |
|------|----------------|--------------|---------------------|---------------------|
| frr  | Ribosome recycling factor (RRF) | Control | 143 | 154 |
| frr  | Ribosome recycling factor (RRF) | Degradation | 137 | 0 |
| yeaZ | Putative protease | Control | 94 | 87 |
| yeaZ | Putative protease | Degradation | 103 | 2* |
| selD | Selenophosphate synthase | Control | 122 | 134 |
| selD | Selenophosphate synthase | Degradation | 115 | 117 |

As shown in Table 1, genes that were modified to encode either the control or degradation tag were transduced into strains that were either ClpX− or ClpX+ using selection of the adjacent drug marker. If the target is essential and ClpXP can degrade it, then a lethal phenotype (no colony formation) is observed (compare dark grey highlight). If the protein is non-essential, then degradation by ClpXP is not lethal (light grey highlight). The asterisk denotes background in this experiment: new phage lysates derived from these colonies gave comparable ratios of transductants indicating that a second-site suppressor can arise during recovery (perhaps a mutation in ClpX or ClpP), but that the YeaZ protein is indeed essential. Note that this is a direct test of the essentiality of the protein gene product and not just the gene.

In another embodiment there is provided a method of degrading a target protein in a cell. The method includes inserting a tag sequence into a target site of the cell chromosome, wherein the tag sequence is YALAA. The tag sequence includes a degradation tag, a drug marker, a 5' flanking region and a 3' flanking region. The 5' and 3' flanking regions include a recognition sequence corresponding to the target site. The method also includes introducing the tag sequence at the end of the target site by recombination, wherein transcription and translation result in a protein containing the degradation tag and the drug marker. The method further includes introducing a protease complex, wherein the complex recognizes and associates with the tag sequence, wherein upon activation of the protease complex the target protein is degraded. In a more particular embodiment, the method is provided wherein the protease complex is ClpXP.

In Vitro Degradation

Figure 6:
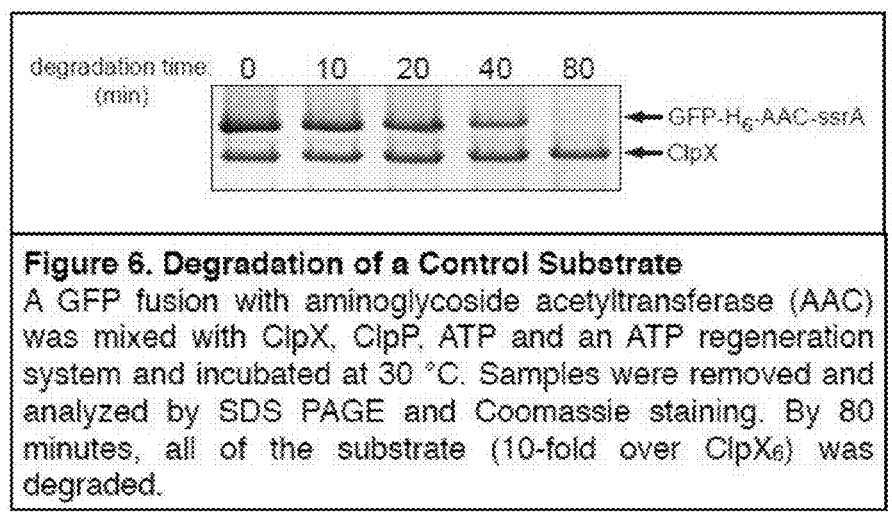
FIG. 6. Degradation of a Control Substrate. A GFP fusion with aminoglycoside acetyltransferase (AAC) was mixed with ClpX, ClpP, ATP and an ATP regeneration system and incubated at 30 degrees C. Samples were removed and analyzed by SDS PAgE and Coomassie staining. By 80 minutes, all of the substrate (10-fold over $ClpX_6$) was degraded.

In FIG. 6, the degradation of a GFP fusion protein is demonstrated. This substrate was used both as a positive control and as a competitor in the degradation studies of the target proteins.

The targeted degradation strategy differs from previous approaches in several aspects, making the methods contained herein be well-suited to interrogate the roles of essential proteins. First, cells are not placed under selective pressure prior to the depletion of the target. Secondly, the method removes the entire target protein from the cell so rogue activities in other regions of the protein will not complicate experiments. Thirdly, this approach can be applied to a wide variety of uncharacterized targets without prior knowledge of the structure, without prior genetics or selection of mutants, and without prior sub-cloning or gene disruption. Finally, as a result of the targeted degradation strategy developed, the ability to purify the target in a native form (along with any interacting partners) using the appended degradation tag and subsequently specifically degrade the target protein (leaving behind any interacting partners) for biochemical studies has been discovered.

Provided in another embodiment herein is a method of identifying the function of protein-coding genes, the method includes performing controlled degradation of cells with target proteins of known function, and performing controlled degradation of cells with proteins of unknown function. The method further includes characterizing and analyzing physiological changes in cells missing proteins of known function, characterizing and analyzing physiological changes in cells missing proteins of unknown function, and evaluating the differences between the two types of cells in order to determine the function of the proteins of unknown function. In one embodiment, the method is provided wherein the protein-coding genes are essential. In an alternative embodiment, the protein-coding genes are nonessential.

In a further embodiment, the method is provided wherein the physiological changes that occur in response to the degradation of proteins of unknown function are compared to a computationally predicted function. This computationally predicted function can act as a control for measuring the changes or differences in the proteins of unknown function which are being degraded. A scientific control is typically used wherein an experimental group and a control group are compared in an experiment. The control group is practically identical to the treatment group, except for the single variable of interest whose effect is being tested. In this case, the control is the computationally predicted function, which is the function that the proteins of unknown function are predicted to perform. Computationally predicted functions are further described in Example 2 below.

In another embodiment, the physiological changes that occur in response to the degradation of proteins of unknown function are compared to the characterization of cells missing essential proteins of known function. Detailed characterization of these cells and observation and analysis of the physiological changes that occur as a result of the degradation of these proteins of unknown function will provide a procedure to allow determination of the subject proteins of unknown function. Such physiological changes may include, but are not limited to growth defects, morphological changes, transcription profiles, and metabolite changes.

EXAMPLES

Example 1

Characterization of growth defects, morphological changes, transcriptional profiles, and metabolite changes in cells missing essential proteins of known function. This set contains 51 target proteins with representatives from major cellular processes and employs the aforementioned targeted degradation technology.

Figure 7:
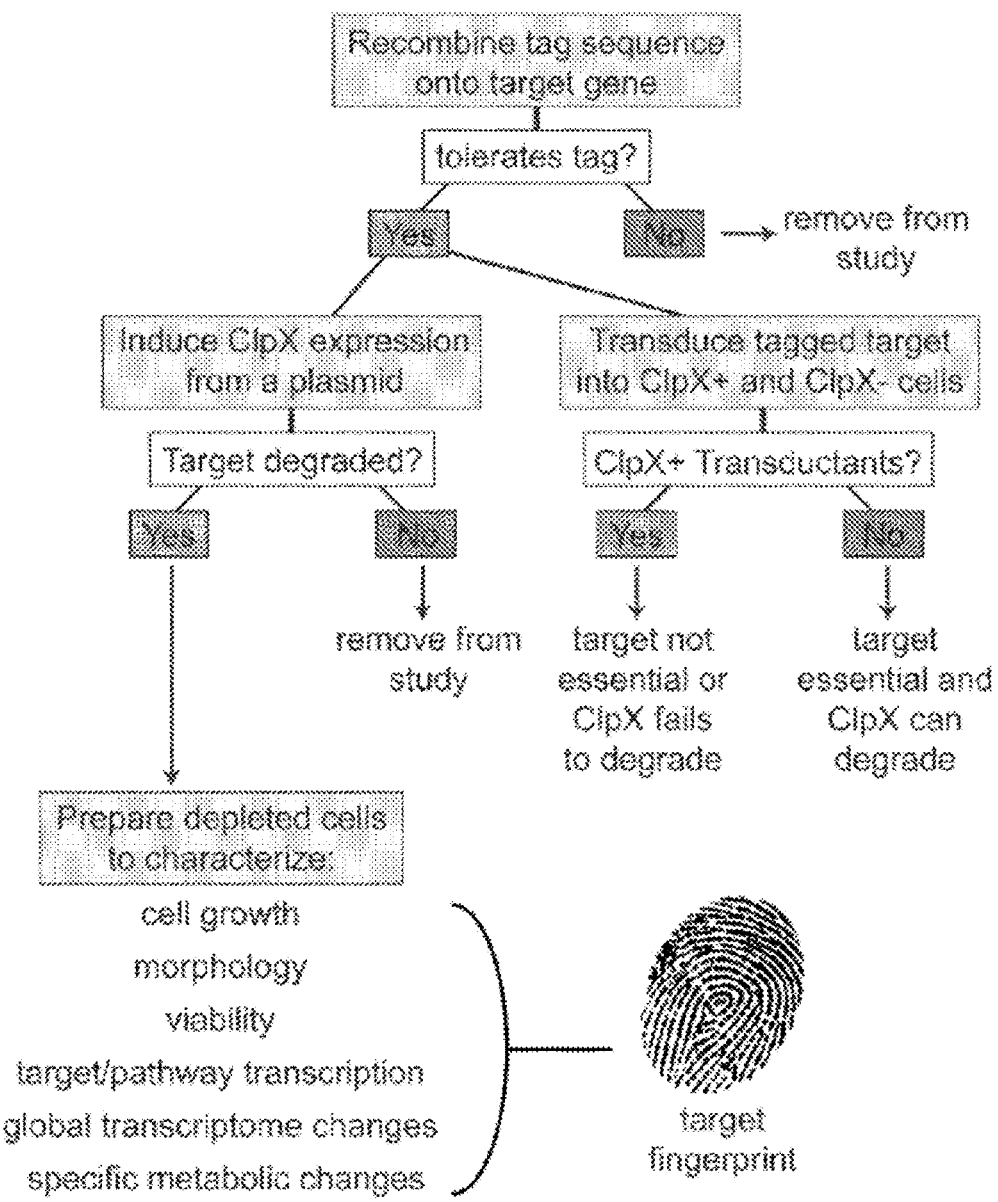
FIG. 7. Experimental Flowchart. The flow chart demonstrates the inventors plan to generate transcriptional, morphological, and biochemical "footprints" of cell behavior in the throws of dealing with the loss of a critical pathway.
Figure 8:
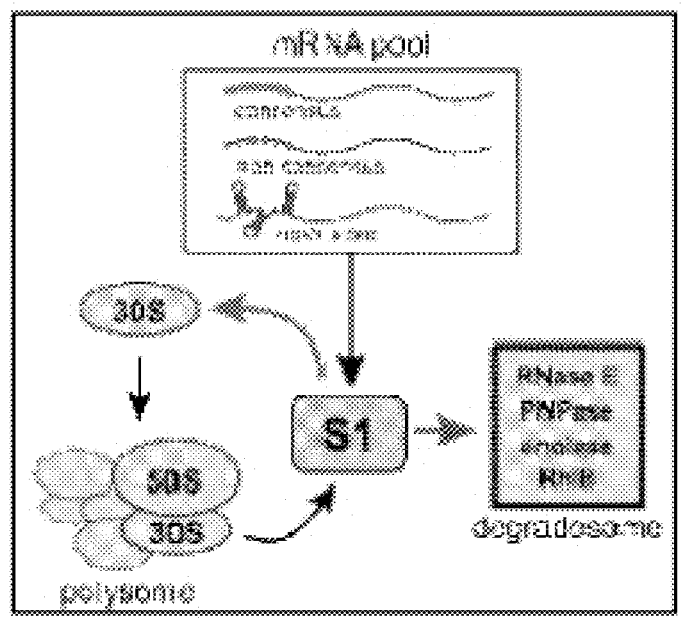
FIG. 8. Ribosomal protein S1 governs mRNA fate. S1 binds to mRNAs and guides them into the translation machinery. Depending on sequence variations near translation initiation sites, S1 binding and release simultaneously controls translation efficiency and entry into the degradosome. An absence of S1 is predicted to destabilize the majority of mRNAs.

The physiology of bacteria is adaptive and changes to energy or metabolite levels promote transcriptional responses that have evolved to restore balance and to deal with stress. Certain embodiments of the present invention enable the observation of the cellular responses to the rapid depletion of essential proteins and enable the generation of a physiology rubric that can be used to compare the responses to the removal of other essential proteins. In one aspect, certain embodiments of the invention allow for the generation of transcriptional, morphological, and biochemical "fingerprints" of cell behavior in response to the loss of a critical pathway (FIG. 7). An exciting aspect of this task is that the inventors will be observing the bacterial responses to the loss of certain essential genes product for the first time.

Using existing databases of *E. coli* gene function and essentiality (PEC, EcoCyc, and EcoGene) (5,6,68), a list of essential proteins that are involved in 16 defined cellular pathways as assigned in the Clusters of Orthologous Groups (COG) database (1,2,69) were assembled. Because some proteins are anticipated to not tolerate the addition of the tags, multiple targets are chosen from each group (except COG-P because there is only one essential cytoplasmic protein). To date, strains with control and degradation tags have been generated on five of these targets (in bold) and additional ones are being generated.

The targets, their COG assignments, and their general functions are as follows: COG-J, translation and ribosome function: map, rpsA, frr, infB, tsf, rluD; COG-K, transcription: rpoB, mc, lexA; COG-L, DNA replication, recombination, and repair: dnaE, ssb, gyrA; COG-D, cell division and chromosome partitioning: ftsZ, mukB, mreB; COG-O, post-translational processing, proteins turnover, chaperones: yeaZ, grpE, groS; COG-M, cell envelope biogenesis, outer membrane: murA, murE, glmS; COG-N, cell motility and secretion: secA, ffh, lpxK; COG-P, inorganic ion transport and metabolism: can; COG-T, signal transduction mechanisms: csrA, spoT, mazE; COG-C, energy production and conversion: fldA, gpsA, ppa; COG-G, carbohydrate transport and metabolism: gapA, suhB, eno; COG-E, amino acid transport and metabolism: asd, prsA, dapA; COG-F, nucleotide transport and metabolism: pyrH, adk, tmk; COG-H, coenzyme metabolism: folA, hemL, ribD, metK; COG-I, lipid metabolism: ispU, fabZ, accC; COG-Q, secondary metabolites, biosynthesis, transport, catabolism: fabG, acpP, fabB. Although YeaZ has only recently been characterized, it is included in this reference set because it interacts with YgjD and YjeE and provides a unique window into a poorly-characterized, essential system in bacteria (38).

The remaining targets of this list are tagged and are tested for essentiality and degradation. The initial characterizations involve growth-rate measurements, characterization of morphology, and viability testing with and without target degradation (induction of ClpX). The growth of strains are tested in parallel with triplicates in 96-well plate format as described (30,70). Common controls are included such as a wild-type strain (no target), and strains with essential targets that can be degraded. These data are compared to the remaining level of target protein at selected times (by immuno-detection) and incorporated to generate a "growth rate per remaining target" profile for each gene.

It is predicted that those proteins directly involved in cell replication (e.g., translation, division septum) will lead to a rapid halt to the culture growth (much like the addition of a translation inhibitor). Alternately, those proteins that are auxiliary (e.g., chaperones) or that are enzymes that produce regulatory compounds or pooled, abundant molecules will continue to divide for a few generations before the toxic effect of removing the essential protein takes effect. It is anticipated that there will also be targets whose depletion provides intermediate results. For example, if the cells switch to a strictly filamentous growth (perhaps by the depletion of FtsZ), the culture turbidity is expected to continue to increase even though the cells have entered a "lethal" situation where colony formation would be prohibited.

Morphology and viability are assessed using both visible and fluorescence microscopy in conjunction with dyes that differentiate between living and dead cells (a mixture of Syto-9 and propidium iodide) as well as dies that detect DNA (DAPI) and membranes (FM4-64). Following these preliminary characterizations, total RNA is isolated from cultures that had the targets degraded as well as their matched control counterparts (11,12,38,71). Depending on the degradation efficiency assessed by immuno-detection, these samples will be taken anywhere from 20-40 minutes after the induction of ClpX. RNA is harvested and characterized "in-house" using Northern blots and quantitative RT-PCR to detect the target protein mRNA as well as other RNAs that is indicative of stress responses. Transcript levels are also measured for genes known to be involved in the same pathway. Finally, the RNA samples are out-sourced for global transcriptome analyses using microarrays.

Example 2

Characterization of Physiological roles and identification of interacting partners of essential proteins of unknown function. This set of 18 target proteins have unknown or poorly-characterized function.

The cellular response to the depletion of a group of poorly-characterized, essential proteins is compared to the responses to the depletion of proteins of known function. Traditional approaches to interrogating such proteins involve depleting the cell of the encoded protein using a sub-cloned version of the gene. Alternately, an investigator may have temperature or cold-sensitive versions that can be conditionally inactivated. Both of these approaches have significant limitations. On the one hand, using cell division to deplete an essential factor to the point that physiologic changes can be observed will also allow for secondary, artifactual changes to occur. For example, if a chaperone no longer assists in the proper folding of a translation factor, one may suggest the chaperone is a translation factor. On the other hand, screening for temperature-sensitive versions in a specific protein may not be feasible, especially considering the target protein has no known function. Rapidly removing these target proteins provides regulatory and biochemical insights by observing the changes to the cell that occur on a short time scale. Additionally, because proteins tend to interact with other factors that are directly related to the same pathway, interacting partners are identified by purifying these targets under native conditions.

Using available online resources of *E. coli* gene function (PEC, EcoCyc, EcoGene) as well as input for EcoGene's curator, inventors have delineated a group of 18 genes that are poorly characterized and that may reveal important, new biochemical pathways. These are: yjeE, ygjD, der, yihA, erpA, yejM, yqgF, nadK, rimN, cohE, ymfT, yhhQ*, yigP*, yagG*, yhbV*, yhhQ*, yraL*, and ybeY*. CohE and ymfT are putative prophage repressors so are not labeled as essential in PEC even though they are "essential" in the Keio collection. For some genes (marked with an asterisk), there are conflicting reports of essentiality. These discrepancies may arise from the growth conditions used or form second-site suppression which will not be an issue with the approach. The experimental approach is similar to that employed in Example 1, but also includes the additional step of purifying the targets under native conditions to identify interacting partners. The changes in growth rate, morphology, viability, and transcription are characterized and compared to those observed in the reference set. After preliminary testing, the entire set of genes are targeted in parallel. Subsequent evaluation of the loss of the target is also evaluated.

Computational predictions of function are incorporated to make preliminary predictions of each target gene's function and the focus is on directly testing for such an activity. For example, degradation of a prophage repressor should lead to induction of the phage which can be revealed in the RT-PCR and microarray data and possibly by observing lysis or phage particle production. As another example, the degradation of YjeE and YgjD are expected to yield similar responses to the degradation of YeaZ because these proteins physically interact in the same pathway (38).

Native target protein complexes are purified cell lysates using the appended $His_6$ tag by binding to nickel-agarose and eluting with imidazole. Additional purification may be achieved by subsequently immune-precipitating the complex or by binding to a column with anti-FLAG antibodies. After preliminary protocol testing, each target is purified in parallel.

Any associated proteins are identified using SDS-PAGE followed by staining. The proteins are identified by excising them from the gel, digesting with trypsin and analyzing the masses of the liberated peptides. Additionally, the eluted sample is inspected using UV-vis spectroscopy to detect nucleic acids or bound co-factors that absorb light. The purified proteins are also tested for covalent modifications using mass spectroscopy. Even if there are no additional factors recovered, the purification allows subsequent study of potential enzymatic function. With some of these target genes, the beginning of the ORF is not clearly determined. Therefore, an added benefit of purifying the protein is that the N-terminus can be identified using mass spectroscopy or N-terminal protein sequencing.

If another complex is discovered with other proteins, the approaches contained herein can be used to specifically degrade the target from the complex in vitro using purified ClpXP (62). This approach allows the inventors to tease apart the specific functionality of the individual components of the complex.

Example 3

Strains with control or degradation tags on S1 are healthy.

A peptide tag sequence that would promote the degradation of S1 by ClpXP, a processive protease complex found in most bacteria, was designed (Baker and Sauer, 2011). A control version of the tag lacked the ClpX recognition determinant and so it prevented unfolding by ClpX and delivery into the proteolytic lumen of ClpP (see Materials and Methods for Examples 3-11). Sequences encoding these tags were recombineered onto the rpsA ORF (encoding S1) in a clpX- strain and selected for their addition using a downstream kanamycin resistance gene (Datta et al., 2006; Sharan et al., 2009). After re-streaking putative $kan^R$ recombinants, PCR was used to confirm the absence of wild-type rpsA, the presence of the tagged versions, and to amplify the region for sequencing. The rpsA-cont and rpsA-deg genes were then transduced using phage P1 into a naive clpX- strain using kanamycin selection and re-verified prior to making stocks.

Figure 9:
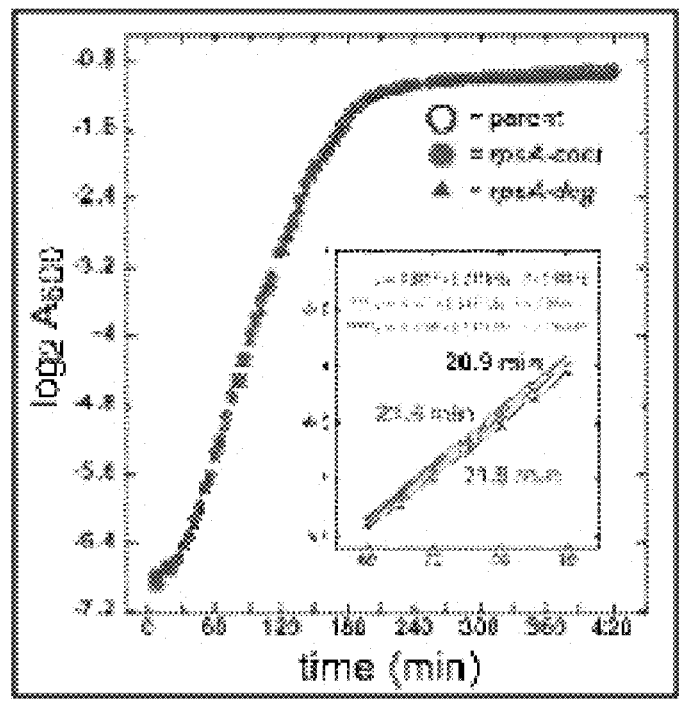
FIG. 9. Peptide tags on the C terminus of S1 do not significantly impair growth. The turbidity of liquid cultures of strains with different forms of S1 were monitored as a function of time at 37° C. Shown are plots of the $log_2$ transforms of the apparent absorbance at 600 nm. The inset shows linear fits to regions of the $log_2$ data with the greatest slopes. Next to each line is the calculated doubling time with the parental in black, rpsA-cont in green, and rpsA-deg in red.

Because S1 is an essential translation factor, the influence of the C-terminal tags on the performance of S1 prior to the planned degradation studies was a factor to be determined. Therefore, the growth of these strains under conditions that allowed for fast doubling times were evaluated when the demand for S1 activity was high and even small defects in translation should influence cell division. FIG. 9 shows the growth of the parental strain (clpX− with wild-type rpsA) and the rpsA-cont and rpsA-deg strains at 37° C. in LB medium supplemented with 0.2% glucose. The growth of the strain with S1-cont was nearly indistinguishable from that of the strain with wild-type S1. The strain with S1-deg showed a slight reduction in growth rate and final culture density. Nonetheless, the appendages on the C-terminus of S1 were practically innocuous.

Example 4

S1 is essential and ClpXP can degrade S1.

P1 lysates were used to transduce rpsA-cont and rpsA-deg into ClpX− and ClpX+ cells by selecting for the adjacent kanamycin resistance marker. In these constructs, there is no region between the tagged rpsA genes and the drug resistance marker that is homologous to the chromosome of the recipient strain, so the tagged rpsA genes always co-transduced with the resistance marker (Moore, 2011). When the rpsA-cont gene was transduced into either a clpX− or clpX+ strain, a comparable number of colonies formed with well over one hundred transductants each depending on the experiment. Therefore, neither the presence of the tag on S1 not the presence of ClpX influenced transduction efficiency. In contrast, when rpsA-deg was transduced into clpX− and clpX+ cells, no colonies arose from the clpX+ recipient whereas hundreds formed from the clpX− strain. This result confirms directly that the protein encoded by rpsA is essential as reported (Kitakawa and Isono, 1982); more importantly, these transduction experiments revealed that the endogenous levels of ClpXP can degrade enough S1-deg to prevent colony formation.

Example 5

ClpP-ClpX expression plasmids were developed that allow controlled degradation of S1-deg.

The host strains herein contain functional ClpP, but no ClpX. In preliminary studies, the degradation of some target substrates were observed, and they exhibited considerable lag upon induction of ClpX from a plasmid. Several measures were taken to reduce background degradation prior to induction and to improve the response time by optimizing the doses of ClpP and ClpX in order to remove S1 in the system as fast as possible (see Methods and Materials for Examples 3-11). Because there was no way of knowing in advance what the optimal doses of ClpP and ClpX would be for this particular target, an empirical selection was used. A library was generated of ClpP-ClpX expression plasmids with the translation initiation sites of both ClpP and ClpX randomized to alter their relative translation efficiencies under full plasmid induction. This expression library was used to transform the rpsA-deg strain and then we screened transformants that harbored plasmids that inhibited the growth of the rpsA-deg strain when induced. Several clones were identified that exhibited a range of colony growth inhibition. Plasmid DNA was recovered from these and used to transform the rpsA-cont strain so relevant growth comparisons could be made.

Figure 10:
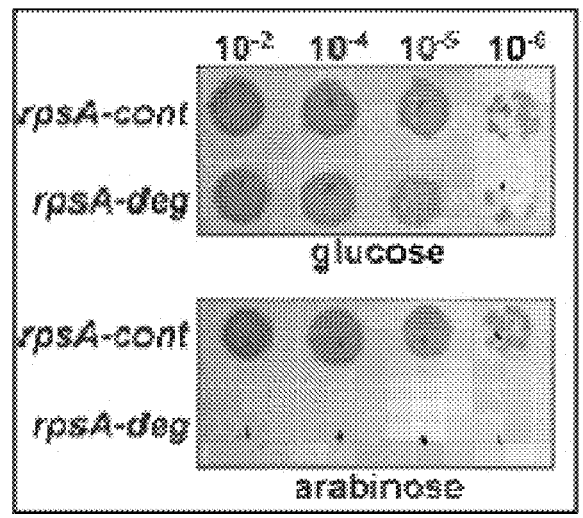
FIG. 10. Expression of ClpP and ClpX from a plasmid inhibits the growth of the rpsA-deg strain. A pair of rpsA-cont and rpsA-deg strains transformed with the same ClpP-X expression plasmid were serially diluted and plated on either glucose (keeping expression off) or arabinose (inducing ClpP and ClpX). Pen marks indicate the locations of culture addition. Colony formation by the rpsA-cont strain was unaffected by ClpP-X expression whereas it was reduced by more than a million fold with the rpsA-deg strain.

Because large liquid cultures of strains undergoing S1 degradation were being sampled, the apparent escape frequency from the degradation event needed to be established so that any potential competitive out-growth of escape mutants could be identified. Therefore, a pair of rpsA-cont and rpsA-deg strains were used, transformed with a pClpP-X expression plasmid that completely inhibited growth when induced to determine the frequency of escape from this selective pressure. Plating these strains under inducing and non-inducing conditions revealed that expression of ClpP-X reduced the number of colony-forming units by more than a million-fold when the strain relied on S1-deg for growth (FIG. 10). The health of wild-type cells harboring this and other pClpP-X plasmids were also evaluated under inducing and non-inducing conditions, and toxicity (by monitoring liquid growth) or changes to protein levels (using SDS-PAGE, not shown) were not observed. Therefore, the reduction in colony formation when ClpP and ClpX were expressed was specifically a consequence of the degradation tag on S1, and escape mutants did not populate cultures at an appreciable frequency prior to induction.

Example 6

Degradation of S1 causes a rapid reduction in growth.

The transduction and plating experiments described above reinforced several published observations that S1 is an essential protein (Briani et al., 2008; Kitakawa and Isono, 1982; Sørensen et al., 1998). What had not heretofore been established is whether the effect S1 has on growth is direct (as a general translation factor) or indirect (in that S1 is required for the production of a particular set of important proteins). By inducing the degradation of S1 at various times during the growth of liquid cultures and monitoring the resulting changes in growth rates, these two possibilities were clarified. It was found herein that f a rapid depletion of S1 caused a rapid reduction in growth, then the function of S1 is directly related to cell division. On the other hand, if rapid S1 depletion caused a gradual reduction in growth, then S1 is probably responsible for the production of stable factors that are important for growth, but these must be depleted through subsequent cell divisions to manifest a pronounced phenotype. For these and all subsequent experiments presented here, a version of the ClpP-X plasmid was employed that significantly inhibited colony formation, but still allowed some growth. The reasons for this choice were that the rpsA-deg strain with this plasmid was easier to work with (strong ClpP-X plasmids caused significant cell death in overnight cultures) and also because a small amount of S1 was presumably present in a functional form.

Figure 11:
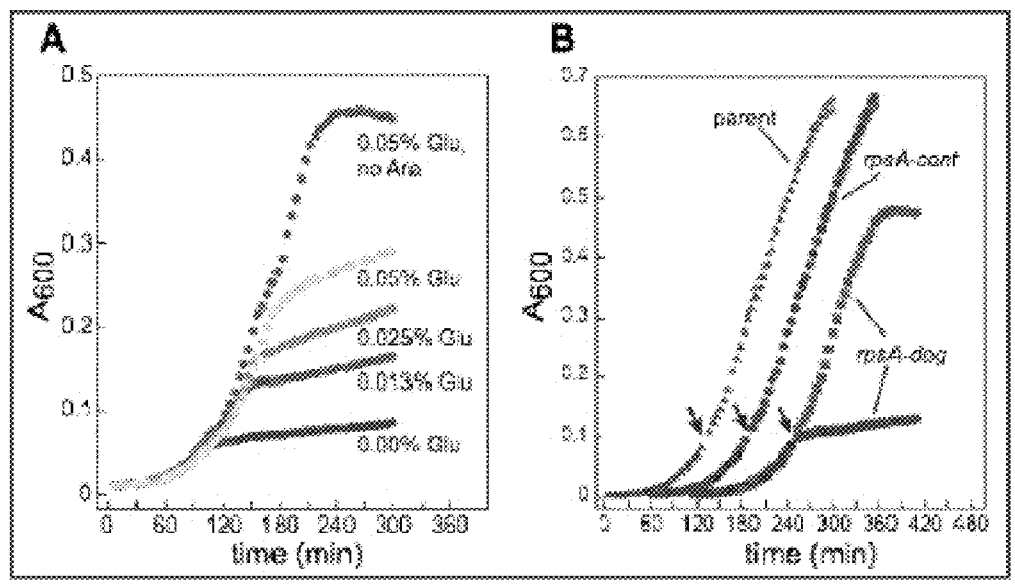
FIG. 11. Degradation of S1 causes an immediate reduction in growth rate. In panel A, the rpsA-deg strain harboring a ClpP-ClpX expression plasmid was diluted into medium containing 0.2% arabinose and increasing amounts of glucose. One culture was grown in glucose without arabinose. As the media depleted of glucose, the cells responded to the presence of arabinose, induced the expression of ClpP-X, and displayed a reduced growth rate. In panel B, duplicates of the parental (triangles), the rpsA-cont (circles), and the rpsA-deg (squares) strains, each transformed with a ClpP-X degradation plasmid, were grown in LB medium with glycerol. One of each set was left uninduced (green) and one was induced with 0.2% arabinose in exponential phase (red). The curves are offset by 60 minutes for clarity. Only expression of ClpP-X in the rpsA-deg strain caused an immediate reduction in growth.

In one experiment, the rpsA-deg strain harboring this ClpP-X expression plasmid was grown in media containing glycerol and varying levels of glucose and arabinose to promote auto-induction of the plasmid (Studier, 2005). When the growth of this strain consumed the preferred glucose carbon source, the cells became responsive to the arabinose and induced the ClpP-X plasmid. The effect of these inductions were sharp reductions in growth rate that were independent of the culture density (FIG. 11, panel A). Upon each induction, a new linear growth rate was achieved, which is consistent with the changes in growth observed when the rpsA gene is repressed (Briani et al., 2008; Sørensen et al., 1998). Keeping in mind that rpsA-deg was still being transcribed and that the selected pClpP-X plasmid did not fully inhibit colony formation, these new growth rates probably reflected a reduced pool of short-lived S1 in the majority of cells, rather than a subset of cells not undergoing S1 depletion (which would have exhibited exponential growth).

The auto-induction experiment demonstrated that a sharp reduction in growth rate was possible at various stages of culture density with the effect being more pronounced at lower cell densities. To more precisely control the induction of the ClpP-X expression plasmid and to assess its effect on the growth of wild-type and control cultures, liquid cultures were manually induced with arabinose at a low cell density when the cultures exhibited a fast, exponential growth. The addition of arabinose had no effect on the growth of cells with wild-type S1 or with S1-cont. In contrast, the growth of the strain with S1-deg was restricted at the next measured time-point (5 minutes after induction), before the cells had appreciably divided (FIG. 11, panel B). Thus, the induction of ClpX-P had an immediate effect on cell division that was dependent on S1 bearing a degradation tag. These induction experiments were done in the absence of glucose, and under these conditions, the uninduced rpsA-deg strain stopped growing at a lower culture density than controls. It is anticipated that there was "leaky" expression from the $P_{BAD}$ promoter controlling ClpP-X in the absence of glucose and the effect on growth became more pronounced as the medium depleted.

Example 7

ClpP-X expression causes a rapid reduction in S1-deg.

A series of manual induction experiments were performed on a larger scale so that the cultures could be sampled for protein and RNA isolation. Mirroring the conditions used in FIG. 11, we sampled cultures in exponential phase prior to induction to establish basal levels of S1 and mRNAs. Arabinose was added to each culture and then two experimental samples were taken five minutes after induction and with subsequent 10-minute intervals (which was a logistic limit). At each time point, one sample was harvested for total protein for use in SDS-PAGE and another was processed for total RNA isolation. The changes in growth of the rpsA-deg strain upon expression of ClpP-X were nearly identical to those observed in the growth experiment shown in FIG. 11, panel B.

Figure 12:
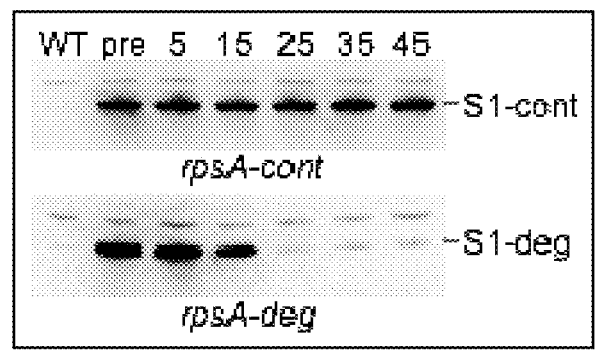
FIG. 12. Degradation of S1-deg upon ClpP-X Expression. Samples of the rpsA-cont and rpsA-deg cultures harboring a ClpP-X expression plasmid were taken at the indicated times (in minutes) relative to the induction with arabinose. Protein samples were resolved by SDS-PAGE and the tagged S1 proteins detected by immunoblotting with anti-FLAG antibodies. A non-specific signal above S1 was also present in the wild-type lanes. The amount of S1-deg protein dropped to very low levels by the 25 minute time point.

Total protein was resolved from each sample and immunoblotting was used to detect the FLAG epitope present in each tag. A protein sample from the culture with wild-type S1 was included in each analysis to highlight a weak, non-specific signal, which was the only other detectable band. The induction of ClpP-X in the rpsA-cont strain did not alter the level of S1-cont throughout the time course, consistent with the observation that the growth of this strain was unaffected by the presence of ClpX (FIG. 12). In contrast, the level of S1-deg was reduced to approximately 50% by 15 minutes and to trace levels at 25 minutes and beyond. When run on the same immunoblot, the signals from the S1-cont and S1-deg in the pre-induction samples were indistinguishable, indicating that the different tag sequences did not significantly alter the basal levels of S1, consistent with their having no appreciable effect on growth (not shown). A standard series of the pre-induced S1-deg sample was prepared by serially diluting it in protein isolated from a wild-type culture. This dilution series was run on an immunoblot with samples from the S1-deg experiment to allow quantification of S1-deg as it depleted. Fitting of the resulting standard curve revealed that the amount of S1-deg present 25, 35, and 45 minutes post induction was less than 0.5% of the level present prior to induction (not shown). In separate experiments, it was observed that this reduction persisted for at least 80 minutes post induction (not shown). Therefore, the cells were unable to compensate for the shortened S1-deg half-life imposed by ClpP-X and remained significantly depleted of S1 once ClpP-X was expressed.

Example 8

S1 depletion causes an increase in rpsA mRNA abundance.

S1 is reported to control its own expression in an auto-regulatory fashion that involves changes in the translation efficiency of its mRNA. Additionally, S1 can influence the stability of other mRNAs, presumably by controlling access to ribosomes (stabilizing messages) and access to the degradosome (responsible for bulk mRNA turnover). To gain insight into the influence of S1 on regulating mRNA pools, specific transcript abundances were measured in parallel samples using quantitative, real-time PCR. Those levels were then compared to the amounts present in wild-type cells and to the levels prior to the expression of ClpP-X to make relative comparisons.

Figure 13:
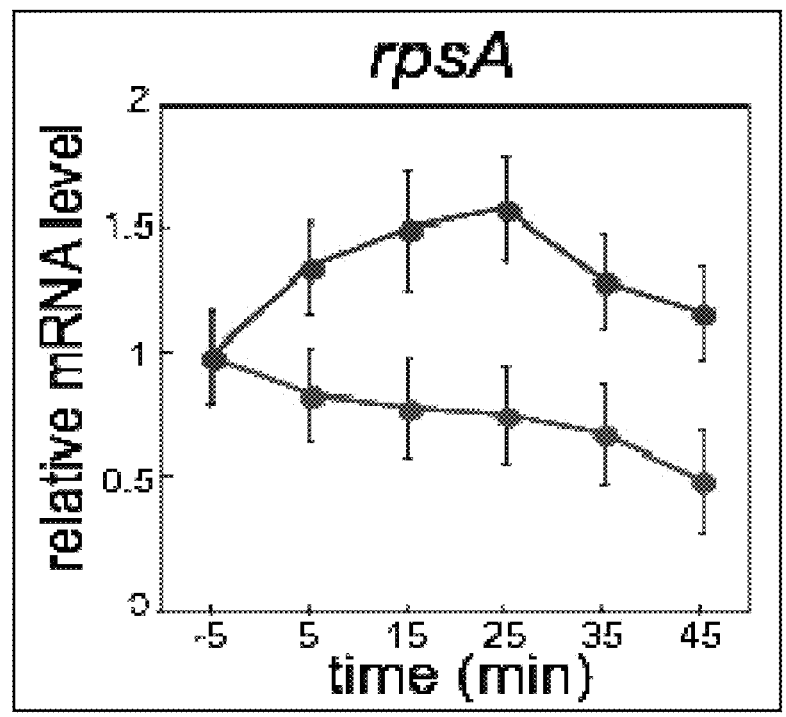
FIG. 13. Changes in rpsA transcript levels upon S1 degradation. Total RNA was isolated from cultures at selected times relative to the induction of ClpP-X and converted to cDNA before the abundance of the rpsA transcript was measured using qPCR. For each time point after induction, the levels were calculated relative to the amount before induction against four different RNA preparations from uninduced cultures and averaged (plotted here) with the error bars indicating the most divergent observations from the average as described in Experimental Procedures. Data from the rpsA-cont culture is in green, and data from the rpsA-deg strain is in red.

In the culture with S1-deg, the amount of rpsA transcript rapidly rose to approximately 1.5 times its original level beginning just five minutes after induction and remained elevated for more than 35 minutes (FIG. 13). In contrast, the amount of this transcript exhibited a slow decline in abundance in the S1-cont culture, which demonstrates that the changes in rpsA-deg mRNA levels were due specifically to S1-deg depletion and not to the increased presence of ClpP or ClpX. The slow decline was observed with several other transcripts that were monitored (described herein) and may reflect normal changes to their abundance as the cells exit exponential phase. Interestingly, when S1 was degraded, the amount of rpsA transcript appeared to increase before the total amount of S1 protein had been significantly reduced. It was identified that degradation of the existing pool of S1 mimicked a global S1 deficiency which, in turn, led to an increase in rpsA transcription. Alternatively, the existing S1 pool may have promoted degradation of a portion of rpsA mRNAs and stripping S1 from them increased their stabilities. As a precaution for this interpretation, the levels of ClpP and ClpX mRNAs were also measured to determine if they had increased by the 5-minute time point. Each transcript was induced approximately 20-fold by 5 minutes and approximately 50 fold by 15 minutes (not shown). Therefore, the timing of the changes observed at 5 minutes was consistent with increased clpP and clpX expression.

The changes in several other transcripts encoding proteins both related and unrelated to S1's established functions are included below. For each case, aside from transcriptional responses, a consideration of S1's ability to simultaneously influence translation initiation and mRNA degradation is warranted. For consistency, the data presented in the following examples were all generated from the same cDNA libraries used for the rpsA mRNA measurements described in FIG. 13.

Example 9

The effect of S1 depletion on mRNAs encoding proteins that directly interact with S1.

The mRNA translation/degradation balancing act is accomplished, in part, by a set of interactions between S1, ribosomal protein S2, RNase E, and PNPase (Bollen et al., 1979; Briani et al., 2008; Feng et al., 2001; Kalapos et al., 1997; Moll et al., 2002a). To determine if S1 depletion in our system influenced the abundances of the mRNAs encoding these factors, transcript levels were measured and compared them to the basal levels observed in control samples.

Figure 14:
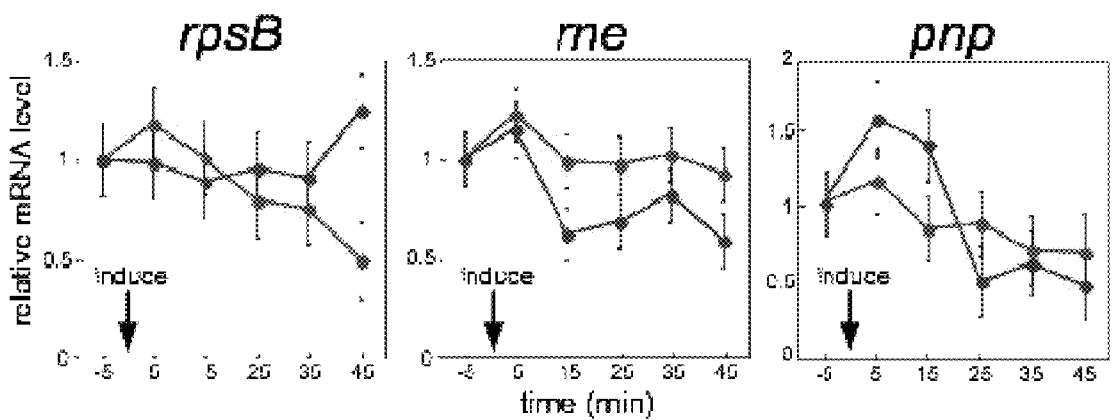
FIG. 14. The levels of mRNAs encoding proteins that interact with S1. The levels of mRNAs encoding S2 (rpsB), RNase E (me), and PNPase (pnp) are shown from rpsA-cont cultures (green) and rpsA-deg cultures (red). the ClpP-X induction time is marked with an arrow.

The level of rpsB transcript (encoding S2) remained essentially the same in both the control and experimental cultures, except for the last time point where the transcript apparently declined in abundance in the control culture and became elevated in the degradation culture. Therefore, a deficiency in S1 did not promote an immediate up-regulation of the gene encoding a component of its binding site on ribosomes nor did it significantly destabilize this transcript (FIG. 14). During S1 depletion, the level of me transcript (encoding RNase E) became reduced to a level that was approximately 75% of its basal value. Likewise, the amount of pnp mRNA (encoding PNPase) also declined moderately in the culture undergoing S1 depletion (FIG. 14). Interestingly, the pnp transcript also exhibited a slight increase in abundance at early time points, similar to the behavior of the rpsA transcript described above. These observations are consistent with previous reports that S1 binding differentially influences the stability the pnp transcript, although the differences seen in these experiments seemed less pronounced than those reported after longer S1 depletions (Briani et al., 2008; Delvillani et al., 2011).

Example 10

The effect of S1 depletion on mRNAs unrelated to S1 function.

S1 depletion was previously reported to cause a striking reduction in the levels of several mRNAs unrelated to S1 function including the monocistronic transcripts from adk, glnS, glyA, and cspE (Briani et al., 2008). Additionally, the stabilization by S1 of the cspE and rpsO transcripts is due specifically to a protection from RNase E (Briani et al., 2008; Delvillani et al., 2011; Régnier and Hajnsdorf, 1991). To gain a broader picture of the influence of S1 on mRNA abundance during our depletion experiments, the transcript levels of cspE and rpsO were measured as well as those from the unrelated ompT, recA, lacI, and lacZ genes which were chosen because they are not under the same regulation as the highly-expressed ribosome and degradosome genes and because they participate in diverse physiological pathways.

Figure 15:
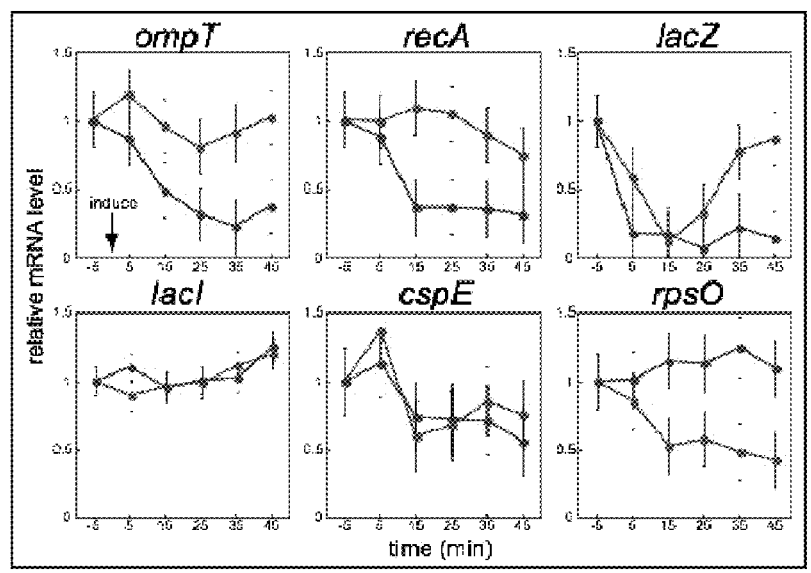
FIG. 15. Transcript levels from genes unrelated to S1 function. Messages in the top row became less abundant upon S1 depletion. Those in the bottom row were either unaffected or increased relative to the control. Data from the rpsA-cont culture is in green, and data from the rpsA-deg strain is in red.

Consistent with the notion that S1 generally stabilizes mRNAs, a reduction in mRNA levels was observed in the S1-deg culture for each of the the ompT, recA, and lacZ transcripts that progressed from the 15-minute time point to a level that was approximately 30% that of the control in each case (FIG. 15, top row). Little difference was observed between the control and experimental samples for lad and cspE and an apparent stabilization of the rpsO transcript throughout the depletion experiment (FIG. 15, bottom row). Therefore, it was found that not all mRNAs are under the stabilizing influence of S1.

Example 11

S1 depletion causes a large decrease in gapA and a large increase in csdA message levels.

Figure 16:
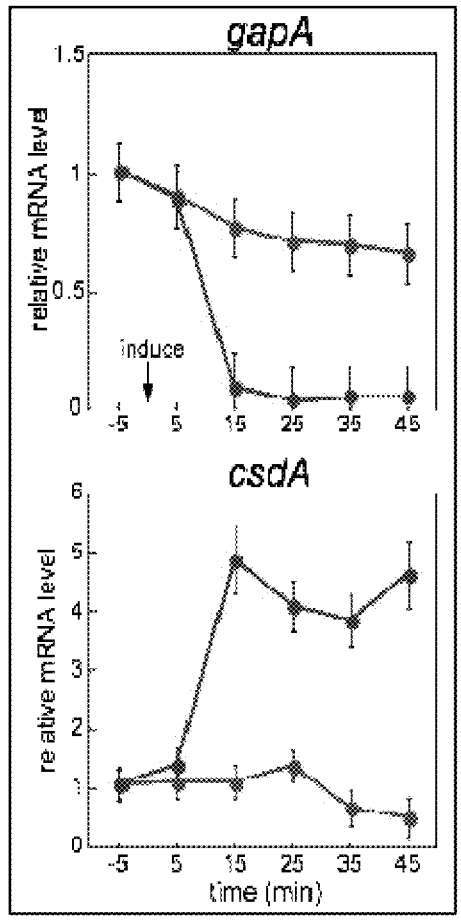
FIG. 16. Transcripts that are highly influenced by the presence of S1. The mRNAs encoding glyceraldehyde phosphate dehydrogenase (gapA) and cold-shock DEAD-box protein A (csdA) exhibited pronounced changes in levels upon S1 depletion. Data from the rpsA-cont culture is in green, and data from the rpsA-deg strain is in red.

Levels of gapA mRNA were also measured (encoding glyceraldehyde 3-phosphate dehydrogenase). This gene has served as an internal standard in many previous RNA regulation studies and expression from its multiple regulated promoters are considered to allow for near-constitutive expression (Charpentier and Branlant, 1994; Seta et al., 1997; Thouvenot et al., 2004; Uliczka et al., 2011). It was discovered herein that the level of this transcript fell sharply at the stage where S1 became noticeably reduced and continued to drop to a level that was less than one twentieth of normal within 25 minutes (FIG. 16). Based on literature reports and on the threshold values in our qPCR measurements, the gapA transcript is normally very abundant and more stable than an average mRNA (Bernstein et al., 2002; Thouvenot et al., 2004). Therefore, this message appears to be unusually sensitive to the presence of S1.

One important factor that is indirectly involved S1 activity is the cold-shock RNA helicase CsdA/DeaD, which was identified as a suppressor of a defective S2 protein (Jones et al., 1996; Toone et al., 1991). This suppression was later traced to a defect in the recruitment of S2 into the small subunit, which, in turn, prevented S1 association (Moll et al., 2002a). Subsequent studies indicated that CsdA is also required for the efficient formation of the large ribosomal subunit at low temperatures (Peil et al., 2008; Shajani et al., 2011). Thus, CsdA appears to be ribosome biogenesis factor that is used to promote the correct folding of the subunit RNAs for robust ribosomal protein association. Considering the intriguing genetic link between CsdA and S1 activity, it was tested herein to determine if the depletion of S1 created a situation that mimicked a defect in ribosome biogenesis and affected the level of the csdA transcript. Of all of the mRNAs tested, the csdA mRNA showed the most pronounced deviance from the unifying trend of a decline in levels upon S1 depletion. At the 15 minute time point (when S1 began to significantly deplete), the amount of csdA message rose sharply to approximately 4 times higher than normal and remained elevated throughout the experiment (FIG. 16). Thus, it appears that S1's differential influence on the fate of certain mRNAs forms a regulatory connection between ribosome assembly (or translation efficiency) and the production of key metabolic factors.

Using a targeted degradation strategy, a unique cellular physiology practically lacking the essential ribosomal protein S1 was created herein. Analysis of changes in selected mRNA transcript levels was a focus to compare the aforementioned system to published reports of S1's influence on message abundance and translation. The findings were consistent with the notion that S1 generally promotes message stability, most likely by allowing entrance into the translation pool wherein mRNAs are protected from the action of RNA degradation machinery. Exceptions to this rule likely reflect either translation-independent regulation or a direct role for S1 in developing the proteome.

The amount of mRNA encoding S1 and PNPase increased at the onset of S1 degradation and then waned after significant S1 depletion. Although the initial increases were relatively small, these changes may have been caused by a stripping of S1 from existing transcripts because they were observed before there was an appreciable reduction in S1. One possibility is that a fraction of these messages are normally destabilized by S1 through a directed delivery to the degradosome. Such a mechanism would allow for a regulation of degradosome production that is coupled to available degradosome activity. Additionally, in this model, the translation of S1 would be balanced such that excess S1 would not accumulate and competitively inhibit general translation initiation. Indeed, the translation of rpsA mRNA is particularly inhibited by excess S1 (Boni et al., 2000; Rasmussen et al., 1993; Skouv et al., 1990).

A comparison of messages under varying regulatory controls revealed that, for the most part, S1 acted to increase their levels despite a wide range of normal abundances. However, in the cases of rpsB, rpsO, lad and cspE, a depletion of S1 had no discernible effect. The lad transcript has long been thought to be under an auto-regulatory control that ensures a constant repressor level (LacR) (Abo et al., 2000; JACOB and MONOD, 1961). The lad ORF contains a LacR binding site near the 3' end that, when occupied, causes premature transcription termination and the production of truncated messages (Abo et al., 2000). When these incomplete messages are translated, the tmRNA quality control system promotes degradation of the nascent LacR protein and promotes mRNA turnover (Abo et al., 2000). Thus, it is predicted that as repressor levels increase, the rate of new repressor synthesis reduced. However, the model of lad auto-repression was recently revisited and it was reinforced that de-repression does not lead to an increase in repressor production as is expected if the gene is under repressor-mediated feedback control (Oehler, 2009).

It was observed that the lad mRNA level remained essentially constant despite a significant perturbation to translation initiation. Culture-to-culture measurements of basal lad mRNA abundance were also very consistent (which led to the smaller error bars for that data set). An increase in lacZ transcript levels was not observed, indicating that LacR levels remained high enough for full repression. It was identified that there is indeed a robust regulatory feature that stabilizes lad mRNA levels. Interestingly, the amount of basal lacZ transcript initially declined in the control as well as the S1-depleted culture, but then recovered to normal levels only in the control. ClpP and ClpX expression should be considered, however the cause of this behavior remains unclear. Also, these cultures were grown in glycerol prior to exposure to arabinose and the changes occurred before detectable S1 depletion, so catabolite regulation may have been influencing lacZ message abundance (Görke and Stülke, 2008).

RpsO and pnp are adjacent genes and, in addition to monocistronic messages for each, a dicistronic mRNA is also produced that is processed by RNase E to regulate PNPase expression (Portier and Regnier, 1984; Régnier and Hajnsdorf, 1991). Therefore, a notable observation from these experiments is that the regions amplified during qPCR from the beginning of the rpsO and pnp ORFs exhibited differential abundances upon S1 depletion. Considering rpsO encodes a ribosomal protein (S15) and that the experimental culture essentially stopped dividing, it is plausible that this medium was not undergoing nutritional depletion to the same extent as the control and this difference may account for some of the observed behavior. Taken together with the concomitant observation that the rpsA and rpsB transcripts were also stable relative to other mRNAs, it is possible that differential mRNA abundance may have accounted for some of the translation bias observed by Sørensen and colleagues when they depleted S1 (Sørensen et al., 1998).

Along with S1, the cold-shock protein CspE was identified as a poly-A binding protein (Feng et al., 2001). Subsequent studies revealed that the cspE message is stabilized from RNase E degradation by S1 and that overexpression of S1 increases this mRNA in the non-translating pool (Delvillani et al., 2011). A drastic reduction in cspE mRNA upon S1 depletion relative to the control was not observed (Briani et al., 2008; Delvillani et al., 2011). The differences in the two observations may stem from the prolonged depletion times in prior studies that could have allowed the activation of additional RNA degradation machinery. Alternatively, in prior S1 depletion experiments multi-copy, plasmid-borne rpsA genes were placed under the control of unnatural promoters, a situation that may have artificially inflated S1 levels (and stabilized mRNAs) prior to experimental depletion.

An unexpected and never heretofore discovered observation was that the abundant gapA transcript dropped rapidly to very low levels. The encoded glyceraldehyde phosphate dehydrogenase couples carbon flow between catabolic and anabolic metabolic pathways and is essential for glycolysis (Seta et al., 1997). Consistent with its central role in cell carbon metabolism, GapA is reported to be constitutively expressed, owing to a collection of promoters that respond to diverse growth conditions (Charpentier and Branlant, 1994; Seta et al., 1997; Thouvenot et al., 2004; Uliczka et al., 2011). Moreover, when transcription is blocked, it is reported that the gapA mRNA is approximately twice as stable as an average mRNA (Bernstein et al., 2002). Considering these facts, it is likely that the gapA message became significantly destabilized in the absence of S1 rather than there being a significant repression of transcription. S1 binding is enhanced by the presence of poly-U and AU-rich regions in the 5' UTRs of several mRNAs, including rpsA itself (Boni et al., 1991; Boni et al., 2000; Hook-Barnard et al., 2007; Skorski et al., 2006) Likewise, the gapA UTR is predicted to contain a significant amount of secondary structure and has several poly-U patches immediately upstream of a poorly-defined Shine Dalgarno sequence (Shultzaberger et al., 2001; Zuker, 2003). Thus, it is likely that this message falls into the category of mRNAs with complex 5'-UTRs that rely on S1 both for stabilization and efficient translation. An awareness of these features and the dramatic changes in transcript levels that were observed herein is warranted when the gapA promoters are employed to drive the expression of reporter genes. It is also noted that the total amount of gapA transcript declined as the control cultures exited from exponential growth (as did several other transcripts that were monitored). Because the measurements were made herein using normalized total RNA, changes in transcript levels were weighted against the highly abundant ribosomal RNA and not necessarily a reflection of abundance relative to all mRNAs.

A final discussion of transcript levels is warranted for the csdA/deaD mRNA, which, unlike other mRNAs, accumulated to high levels upon S1 depletion. This gene encodes a DEAD-box RNA helicase, a cold-shock factor that assists in the maturation of the large ribosomal subunit and also in enhancing the incorporation of S2 (which aids in S1 binding) (Jones et al., 1996; Moll et al., 2002a; Peil et al., 2008; Phadtare and Severinov, 2010; Shajani et al., 2011)(Phadtare review). When induced, CsdA is found both associated with ribosomes and as a component of the degradosome in place of the usual RhlB helicase (Prud'homme-Généreux et al., 2004). At first glance, the inverse relationship between S1 abundance and csdA transcript levels suggests that S1 deficiency is functionally interpreted by the cell as a cold shock. Because no natural mechanism causing significant S1 depletion has been identified, the observed response is likely indicative of an increase in secondary structure of a regulatory RNA that S1 normally either destabilizes or occludes (Jones et al., 1996).

S1 is one of the few ribosomal proteins that has assigned functions; a feature that has no doubt been driven by the ability to be stripped from the small subunit prior to in vitro studies. As a result of that which has been provided in this disclosure, S1 deficiency can now be experimentally addressed either in vivo or in vitro by selectively targeting and degrading it specifically. These preliminary studies reveal that the response to S1 depletion on the abundance of mRNAs was largely predictable: in the absence of translation, many mRNAs are more prone to degradation. It is well-established that translation activity is correlated with mRNA abundance; however, changes in protein synthesis rates rarely scale linearly with changes in transcript levels. The way in which S1 shapes the production of an appropriate proteome from an available transcriptome will be discussed herein. With the ClpP-X plasmid which has been used herein, the S1-depleted cultures still undergo cell division, indicating that some translation is occurring. In this situation, it is predicted that mRNAs with the highest specific activities were being preferentially decoded. Rather than following a pick-and-choose approach with favored transcripts, technological advances now permit a global quantification of all mRNAs as well as determinations of their translation efficiencies to be investigated en mass upon S1 depletion (Cho et al., 2009; Mendoza-Vargas et al., 2009; Raghavan et al., 2011; Yoder-Himes et al., 2009). Such a holistic strategy, coupled with computational sequence analyses, provides a comprehensive picture of S1's influence on translation.

Aside from its usefulness in interrogating S1, the optimized degradation approach employed herein is be broadly applicable in the study of both essential and non-essential proteins. To date, more than 10 other essential proteins have been targeted for conditional degradation using the system and methods disclosed herein. Because most other cases do not involve the destruction of a central mRNA regulatory factor, the initial changes in transcript and metabolite levels upon rapid depletion of a particular target are unique to any given perturbed biochemical pathway. By monitoring such cell reflexes, an unprecedented insight can be gained into what a cell "thinks" is occurring as an important system shuts down.

Methods and Materials for Examples 3-11

Strains and Culture Conditions

Recombineering to add the control and degradation tags was performed in strain SM1405 (X90, clpX−, clpA−, ma−, with pSIM-5) (Datta et al., 2006; Hayes et al., 2002). These loci were then transduced with phage P1 by selecting for the adjacent kanamycin resistance markers into G78 (BW30270, an fnr+, rph+ derivative of MG1655, with both the clpX and ma ORFs replaced by FRT recombination sites, and the araBA ORFs replaced with a chloramphenicol resistance marker). The presented growth studies were performed using LB supplemented with 0.2% glycerol and either 0.2% glucose or 0.2% arabinose as indicated. The pClpP-X plasmid was maintained with 125 ug/mL of ampicillin.

Construction of rpsA Encoding Control and Degradation Peptide Tags on S1

Figure 17:
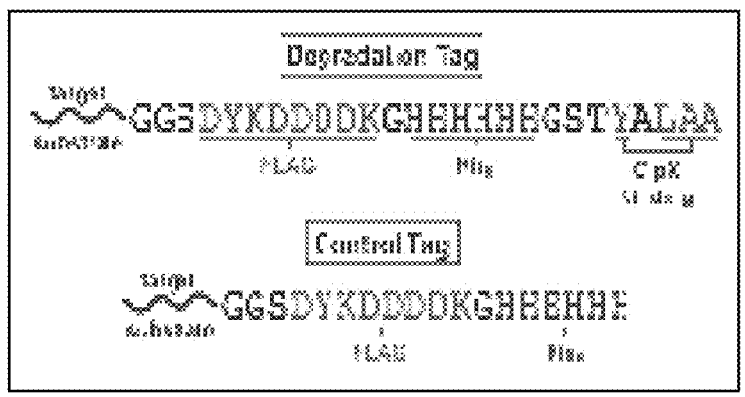
FIG. 17. The control and degradation tags. A degradation peptide tag (SEQ ID NO:2) contains a ClpX recognition determinant (red residues) as well as the FLAG (green), $His_6$ (blue), and flexible linker segments. The control tag (SEQ ID NO:3) lacks the ClpX determinant and is encoded by the same DNA sequence as the degradation tag except a stop codon replaces the glycine codon after the $His_6$ tag.

A C-terminal peptide tag was designed that would be useful in directing a wide range of protein substrates into ClpXP. Key features of the tag include flexible linkers separating functional elements that project the ClpX recognition determinants far enough away from the substrate for efficient engagement by the protease. Two epitopes were included into the sequence to aid in detection and purification (FIG. 17). The position of the FLAG epitope adjacent to the body of the substrate is important: the distance from the pore of ClpX to the proteolytic lumen of ClpP is approximately 40 amino acids (Kenniston et al., 2005; Lee et al., 2001; Martin et al., 2008; Moore et al., 2008). Therefore, disappearance of the FLAG epitope indicates that ClpXP had full-engaged and translocated well into the body of the substrate. The sequence encoding the tag was assembled using sequential PCR reactions that positioned the tag sequence next to an ORF encoding aminoglycoside acetyltransferase, which confers kanamycin resistance. The assemblage was then amplified to append sequences homologous to the regions flanking the stop codon of rpsA. Lambda RED-mediated recombineering was used to incorporate the tag sequences on the 3' end of the chromosomal rpsA gene (Datta et al., 2006). This kan$^R$ construct has no promoter and relies on transcription of rpsA to generate a polycistronic message to confer resistance.

Growth Analysis

Overnight cultures of test strains were diluted 1/100 in fresh medium and 3-5 individual 100 µL samples were aliquoted into the central wells of a 96 well plate. The outer wells were filled with water and the plates incubated at 37° C. with continuous shaking in a Biotek Synergy MX plate reader. Culture turbidity was measured every 5 minutes and the resulting data from each well was averaged. For manual inductions, the plate reader was paused, sugars were added, and then measurements were resumed within one minute. Growth rates were determined by transforming the raw data into $\log_2$ and using the derivative to establish the steepest log-linear range. Linear regression was then used on that region of the $\log_2$ data and the doubling time calculated from the inverse slope (Monod, 1949).

Design and Selection of ClpX-P Expression Plasmids

We reasoned that a substantial portion of the existing pool of ClpP may be occupied with ClpA and unavailable for ClpX-mediated degradation. While a clpA− strain could be used, ClpAP degrades and lowers the level of ssrA-tagged substrates, which are competitive inhibitors of the degradation of our intended S1-deg target by ClpXP (Flynn et al., 2001; Gottesman et al., 1998; Lies and Maurizi, 2008). Therefore, without knowing the relative exchange rates of ClpA and ClpX for access to ClpP, additional ClpP was expressed at the same time as ClpX was induced. ClpP and ClpX were PCR-amplified from E. coli genomic DNA using primers that introduced random nucleotides at two positions in the Shine-Dalgarno sequences of each gene. PCR was then used to fuse the genes together to restore the arrangement found in the operon and cloned under control of the $P_{araBAD}$ promoter in a plasmid containing araC, bla, and the pBR322 origin. After selection on ampicillin, the transformed colonies were pooled in liquid medium, harvested, and a plasmid miniprep was then prepared of the mixed library. Strain G115 containing a degradation tag on S1 was transformed with the library and recovered in LB containing 0.2% glucose. After overnight colony selection on a glucose-ampicillin plate, individual colonies were picked with toothpicks and re-streaked onto ampicillin plates with either glucose or arabinose and incubated overnight. Streaks showing noticeable growth inhibition on arabinose were used to identify candidate clones. These strains were picked from the corresponding glucose plate and grown to early stationary phase in glycerol-glucose-ampicillin medium. Serial dilutions of each were then made in unmodified, ice-cold LB and spotted onto ampicillin plates with glucose or arabinose to allow individual colony development. The toxicity of the induced plasmids were then noted and minipreps of each were used to transform a strain with a control tag on S1. All strains were maintained in glucose medium and starvation periods were avoided to reduce unintentional ClpP-X expression.

S1 Degradation and Sample Preparation

Overnight cultures of the control and degradation strains were diluted 1/100 into ampicillin-glycerol medium and grown at 37° C. with aeration. At when the cultures were in exponential phase growth, uninduced samples were withdrawn and then 0.2% arabinose was added to induce ClpP-X expression. At 10 minute intervals, individual samples were taken for turbidity measurements, for total protein recovery, and for RNA isolation. The samples for protein analysis were mixed with ice-cold protease-inhibitor cocktail (Roche) prior to harvesting at 4° C. and the cells then lysed in B-Per2 (Pierce) supplemented with 1 mM EDTA and 0.1 mg/mL lysozyme. After lysis, the samples were supplemented with an equal volume of a mixture containing 25 mM K-HEPES, 5 mM $MgCl_2$, and 10 µL/mL Benzonase (Sigma) and incubated an additional 5 minutes. Volumes were adjusted to normalize each sample according to the turbidity of the cultures when harvested and an aliquot of each mixed with SDS sample buffer and heated prior to electrophoresis. Total RNA was prepared following slight modifications to established protocols (Bernstein et al., 2002; Kingston et al., 2001; Xu et al., 2011), quantified spectrophotometrically, and adjusted to a 1 mg/mL in 10 mM bis-Tris, 0.1 mM EDTA, pH 6.5 prior to storage at −80° C.

mRNA Quantification

A commercial random-priming kit was used to prepare cDNA from 0.5 µg of each RNA sample (iScript, Bio-Rad) and then each library was diluted 4-fold in water and stored at −80° C. Quantitative PCR was performed using primers that amplified ~100-120 by segments from the extreme 5' ends of each gene's ORF with a commercial mixture of buffer, fluorescent dye, and polymerase (SsoFast, Bio-Rad). Amplification was carried out and recorded using a Bio-Rad MiniOpticon detection system. Rare transcripts were quantified without further dilution of the cDNAs and abundant transcripts were quantified following an additional 20-fold dilution. The raw data from the amplifications were analyzed in spreadsheets after baseline optimizations to assign cycle thresholds with a higher degree of accuracy than the onboard software prior to averaging replicates (Ruijter et al., 2009). Error boundaries were assigned for each data point by combining three measurements: (i) the variance in the measurement of a single transcript following six independent qPCR measurements from the same cDNA sample (which established error from mixing); (ii) the difference between abundance calculations using the in-well amplification efficiency versus the averaged efficiency for each target (which accounts for deviance in slope calculations); and (iii), the difference in apparent relative abundance to uninduced samples when the experimental cycle thresholds were separately compared against the basal thresholds obtained from different cultures. The latter measurement also allowed for an error estimate of the amount of basal transcript present in the uninduced samples (to which all others in a series were compared) and accounted for the most of the observed variances.

REFERENCES

1. Baba T., T. Ara, M. Hasegawa, Y. Takai, Y. Okumura, M. Baba, K. A. Datsenko, M. Tomita, B. L. Wanner, and H. Mori. 2006. Construction of *Escherichia coli* K-12 in-frame, single-gene knockout mutants: the Keio collection. Mol Syst Biol 2:2006.0008.
2. Gerdes S. Y., M. D. Scholle, J. W. Campbell, G. Balazsi, E. Ravasz, M. D. Daugherty, A. L. Somera, N. C. Kyrpides, I. Anderson, M. S. Gelfand, A. Bhattacharya, V. Kapatral, M. D'Souza, M. V. Baev, Y. Grechkin, F. Mseeh, M. Y. Fonstein, R. Overbeek, A. L. Barabasi, Z. N. Oltvai, and A. L. Osterman. 2003. Experimental determination and system level analysis of essential genes in *Escherichia coli* MG1655. J Bacteriol 185:5673-5684.
3. Hemm M. R., B. J. Paul, J. Miranda-Rios, A. Zhang, N. Soltanzad, and G. Storz. 2010. Small stress response proteins in *Escherichia coli*: proteins missed by classical proteomic studies. J Bacteriol 192:46-58.
4. Hobbs E. C., J. L. Astarita, and G. Storz. 2010. Small RNAs and small proteins involved in resistance to cell envelope stress and acid shock in *Escherichia coli*: analysis of a bar-coded mutant collection. J Bacteriol 192:59-67.
5. Rudd K. E. 2000. EcoGene: a genome sequence database for *Escherichia coli* K-12. Nucleic Acids Res 28:60-64.
6. Yamazaki Y., H. Niki, and J. Kato. 2008. Profiling of *Escherichia coli* Chromosome database. Methods Mol Biol 416:385-389.
7. Conrad T. M., A. R. Joyce, M. K. Applebee, C. L. Barrett, B. Xie, Y. Gao, and B. Ø. Palsson. 2009. Whole-genome resequencing of *Escherichia coli* K-12 MG1655 undergoing short-term laboratory evolution in lactate minimal media reveals flexible selection of adaptive mutations. Genome Biol 10:R118.
8. Fong S. S., A. Nanchen, B. O. Palsson, and U. Sauer. 2006. Latent pathway activation and increased pathway capacity enable *Escherichia coli* adaptation to loss of key metabolic enzymes. J Biol Chem 281:8024-8033.
9. Herring C. D., A. Raghunathan, C. Honisch, T. Patel, M. K. Applebee, A. R. Joyce, T. J. Albert, F. R. Blattner, D. van den Boom, C. R. Cantor, and B. Ø. Palsson. 2006. Comparative genome sequencing of *Escherichia coli* allows observation of bacterial evolution on a laboratory timescale. Nat Genet 38:1406-1412.
10. Ideker T., V. Thorsson, J. A. Ranish, R. Christmas, J. Buhler, J. K. Eng, R. Bumgarner, D. R. Goodlett, R. Aebersold, and L. Hood. 2001. Integrated genomic and proteomic analyses of a systematically perturbed metabolic network. Science 292:929-934.
11. Ishii N., K. Nakahigashi, T. Baba, M. Robert, T. Soga, A. Kanai, T. Hirasawa 12. Joyce A. R., J. L. Reed, A. White, R. Edwards, A. Osterman, T. Baba, H. Mori, S. A. Lesely, B. Ø. Palsson, and S. Agarwalla. 2006. Experimental and computational assessment of conditionally essential genes in *Escherichia coli*. J Bacteriol 188:8259-8271.
13. Vemuri G. N., and A. A. Aristidou. 2005. Metabolic engineering in the -omics era: elucidating and modulating regulatory networks. Microbiol Mol Biol Rev 69:197-216.
14. Glass J. I., N. Assad-Garcia, N. Alperovich, S. Yooseph, M. R. Lewis, M. Maruf, C. A. Hutchison, H. O. Smith, and J. C. Venter. 2006. Essential genes of a minimal bacterium. Proc Natl Acad Sci USA 103:425-430.
15. Hutchison C. A., S. N. Peterson, S. R. Gill, R. T. Cline, O. White, C. M. Fraser, H. O. Smith, and J. C. Venter. 1999. Global transposon mutagenesis and a minimal Mycoplasma genome. Science 286:2165-2169.
16. Mushegian A. R., and E. V. Koonin. 1996. A minimal gene set for cellular life derived by comparison of complete bacterial genomes. Proc Natl Acad Sci USA 93:10268-10273.
17. Fleischmann R. D., M. D. Adams, O. White, R. A. Clayton, E. F. Kirkness, A. R. Kerlavage, C. J. Bult, J. F. Tomb, B. A. Dougherty, and J. M. Merrick. 1995. Whole-genome random sequencing and assembly of Haemophilus influenzae Rd. Science 269:496-512.
18. Fraser C. M., J. D. Gocayne, O. White, M. D. Adams, R. A. Clayton, R. D. Fleischmann, C. J. Bult, A. R. Kerlavage, G. Sutton, J. M. Kelley, R. D. Fritchman, J. F. Weidman, K. V. Small, M. Sandusky, J. Fuhrmann, D. Nguyen, T. R. Utterback, D. M. Saudek, C. A. Phillips, J. M. Merrick, J. F. Tomb, B. A. Dougherty, K. F. Bott, P. C. Hu, T. S. Lucier, S. N. Peterson, H. O. Smith, C. A. Hutchison, and J. C. Venter. 1995. The minimal gene complement of Mycoplasma genitalium. Science 270:397-403.
19. Kobayashi K., S. D. Ehrlich, A. Albertini, G. Amati, K. K. Andersen, M. Arnaud, K. Asai, S. Ashikaga, S. Aymerich, P. Bessieres, F. Boland, S. C. Brignell, S. Bron, K. Bunai, J. Chapuis, L. C. Christiansen, A. Danchin, M. Débarbouille, E. Dervyn, E. Deuerling, K. Devine, S. K. Devine, O. Dreesen, J. Errington, S. Fillinger, S. J. Foster, Y. Fujita, A. Galizzi, R. Gardan, C. Eschevins, T. Fukushima, K. Haga, C. R. Harwood, M. Hecker, D.

Hosoya, M. F. Hullo, H. Kakeshita, D. Karamata, Y. Kasahara, F. Kawamura, K. Koga, P. Koski, R. Kuwana, D. Imamura, M. Ishimaru, S. Ishikawa, I. Ishio, D. Le Coq, A. Masson, C. Mauël, R. Meima, R. P. Mellado, A. Moir, S. Moriya, E. Nagakawa, H. Nanamiya, S. Nakai, P. Nygaard, M. Ogura, T. Ohanan, M. O'Reilly, M. O'Rourke, Z. Pragai, H. M. Pooley, G. Rapoport, J. P. Rawlins, L. A. Rivas, C.

Rivolta, A. Sadaie, Y. Sadaie, M. Sarvas, T. Sato, H. H. Saxild, E. Scanlan, W. Schumann, J. F. Seegers, J. Sekiguchi, A. Sekowska, S. J. Séror, M.
Simon, P. Stragier, R. Studer, H. Takamatsu, T. Tanaka, M. Takeuchi, H. B. Thomaides, V. Vagner, J. M. van Dijl, K. Watabe, A. Wipat, H. Yamamoto, M. Yamamoto, Y. Yamamoto, K. Yamane, K. Yata, K. Yoshida, H. Yoshikawa, U. Zuber, and N. Ogasawara. 2003. Essential *Bacillus subtilis* genes. Proc Natl Acad Sci USA 100:4678-4683.

20. Kunst F., N. Ogasawara, I. Moszer, A. M. Albertini, G. Alloni, V. Azevedo, M. G. Bertero, P. Bessiéres, A. Bolotin, S. Borchert, R. Borriss, L. Boursier, A. Brans, M. Braun, S. C. Brignell, S. Bron, S. Brouillet, C. V. Bruschi, B. Caldwell, V. Capuano, N. M. Carter, S. K. Choi, J. J. Codani, I. F. Connerton, and A. Danchin. 1997. The complete genome sequence of the gram-positive bacterium *Bacillus subtilis*. Nature 390:249-256.

21. Sassetti C. M., D. H. Boyd, and E. J. Rubin. 2001. Comprehensive identification of conditionally essential genes in mycobacteria. Proc Natl Acad Sci USA 98:12712-12717.

22. Sassetti C. M., D. H. Boyd, and E. J. Rubin. 2003. Genes required for mycobacterial growth defined by high density mutagenesis. Mol Microbiol 48:77-84.

23. Liberati N. T., J. M. Urbach, S. Miyata, D. G. Lee, E. Drenkard, G. Wu, J. Villanueva, T. Wei, and F. M. Ausubel. 2006. An ordered, nonredundant library of *Pseudomonas aeruginosa* strain PA14 transposon insertion mutants. Proc Natl Acad Sci USA 103:2833-2838.

24. Wong S. M., and J. J. Mekalanos. 2000. Genetic footprinting with mariner-based transposition in *Pseudomonas aeruginosa*. Proc Natl Acad Sci USA 97:10191-10196.

25. Jenks P. J., C. Chevalier, C. Ecobichon, and A. Labigne. 2001. Identification of nonessential *Helicobacter pylori* genes using random mutagenesis and loop amplification. Res Microbiol 152:725-734.

26. Kwon Y. M., L. F. Kubena, D. J. Nisbet, and S. C. Ricke. 2003. Isolation of *Salmonella typhimurium* Tn5 mutants defective for survival on egg shell surface using transposon footprinting. J Environ Sci Health B 38:103-109.

27. Tong X., J. W. Campbell, G. Balázsi, K. A. Kay, B. L. Wanner, S. Y. Gerdes, and Z. N.
Oltvai. 2004. Genome-scale identification of conditionally essential genes in *E. coli* by DNA microarrays. Biochem Biophys Res Commun 322:347-354.

28. Altuvia S. 2007. Identification of bacterial small noncoding RNAs: experimental approaches. Curr Opin Microbiol 10:257-261.

29. Livny J., and M. K. Waldor. 2007. Identification of small RNAs in diverse bacterial species. Curr Opin Microbiol 10:96-101.

30. Herring C. D., and F. R. Blattner. 2004. Conditional lethal amber mutations in essential *Escherichia coli* genes. J Bacteriol 186:2673-2681.

31. Britton R. A. 2009. Role of GTPases in bacterial ribosome assembly. Annu Rev Microbiol 63:155-176.

32. Connolly K., J. P. Rife, and G. Culver. 2008. Mechanistic insight into the ribosome biogenesis functions of the ancient protein KsgA. Mol Microbiol 70:1062-1075.

33. O'Farrell H. C., Z. Xu, G. M. Culver, and J. P. Rife. 2008. Sequence and structural evolution of the KsgA/Dim1 methyltransferase family. BMC Res Notes 1:108.

34. Sergiev P. V., A. A. Bogdanov, and O. A. Dontsova. 2007. Ribosomal RNA guanine-(N2)-methyltransferases and their targets. Nucleic Acids Res 35:2295-2301.

35. Marchler-Bauer A., J. B. Anderson, F. Chitsaz, M. K. Derbyshire, C. DeWeese-Scott, J. H. Fong, L. Y. Geer, R. C. Geer, N. R. Gonzales, M. Gwadz, S. He, D. I. Hurwitz, J. D. Jackson, Z. Ke, C. J. Lanczycki, C. A. Liebert, C. Liu, F. Lu, S. Lu, G. H. Marchler, M. Mullokandov, J. S. Song, A. Tasneem, N. Thanki, R. A. Yamashita, D. Zhang, N. Zhang, and S. H. Bryant. 2009. CDD: specific functional annotation with the Conserved Domain Database. Nucleic Acids Res 37:D205-D210.

36. de Sousa Abreu R., L. O. Penalva, E. M. Marcotte, and C. Vogel. 2009. Global signatures of protein and mRNA expression levels. Mol Biosyst 5:1512-1526.

37. Traxler M. F., S. M. Summers, H. T. Nguyen, V. M. Zacharia, G. A. Hightower, J. T. Smith, and T. Conway. 2008. The global, ppGpp-mediated stringent response to amino acid starvation in *Escherichia coli*. Mol Microbiol 68:1128-1148.

38. Handford J. I., B. Ize, G. Buchanan, G. P. Butland, J. Greenblatt, A. Emili, and T. Palmer. 2009. Conserved network of proteins essential for bacterial viability. J Bacteriol 191:4732-4749.

39. Akiyama Y. 2009. Quality control of cytoplasmic membrane proteins in *Escherichia coli*. J Biochem 146:449-454.

40. Baker T. A., and R. T. Sauer. 2006. ATP-dependent proteases of bacteria: recognition logic and operating principles. Trends Biochem Sci 31:647-653.

41. Hoskins J. R., S. Sharma, B. K. Sathyanarayana, and S. Wickner. 2001. Clp ATPases and their role in protein unfolding and degradation. Adv Protein Chem 59:413-429.

42. Van Melderen L., and A. Aertsen. 2009. Regulation and quality control by Lon-dependent proteolysis. Res Microbiol 160:645-651.

43. Zolkiewski M. 2006. A camel passes through the eye of a needle: protein unfolding activity of Clp ATPases. Mol Microbiol 61:1094-1100.

44. Martin A., T. A. Baker, and R. T. Sauer. 2008. Diverse pore loops of the AAA+ ClpX machine mediate unassisted and adaptor-dependent recognition of ssrA-tagged substrates. Mol Cell 29:441-450.

45. Martin A., T. A. Baker, and R. T. Sauer. 2008. Protein unfolding by a AAA+ protease is dependent on ATP-hydrolysis rates and substrate energy landscapes. Nat Struct Mol Biol 15:139-145.

46. Martin A., T. A. Baker, and R. T. Sauer. 2008. Pore loops of the AAA+ ClpX machine grip substrates to drive translocation and unfolding. Nat Struct Mol Biol 15:1147-1151.

47. Shin Y., J. H. Davis, R. R. Brau, A. Martin, J. A. Kenniston, T. A. Baker, R. T. Sauer, and M. J. Lang. 2009. Single-molecule denaturation and degradation of proteins by the AAA+ ClpXP protease. Proc Natl Acad Sci USA 106: 19340-19345.

48. Szyk A., and M. R. Maurizi. 2006. Crystal structure at 1.9A of *E. coli* ClpP with a peptide covalently bound at the active site. J Struct Biol 156:165-174.

49. Wang J., J. A. Harding, and J. M. Flanagan. 1997. The structure of ClpP at 2.3 A resolution suggests a model for ATP-dependent proteolysis. Cell 91:447-456.

50. Jennings L. D., D. S. Lun, M. Médard, and S. Licht. 2008. ClpP hydrolyzes a protein substrate processively in the absence of the ClpA ATPase: mechanistic studies of ATPindependent proteolysis. Biochemistry 47:11536-11546.

51. Gottesman S., E. Roche, Y. Zhou, and R. T. Sauer. 1998. The ClpXP and ClpAP proteases degrade proteins with carboxy-terminal peptide tails added by the SsrA-tagging system. Genes Dev 12:1338-1347.

52. Karzai A. W., M. M. Susskind, and R. T. Sauer. 1999. SmpB, a unique RNA-binding protein essential for the peptide-tagging activity of SsrA (tmRNA). EMBO J 18:3793-3799.

53. Keiler K. C., P. R. Waller, and R. T. Sauer. 1996. Role of a peptide tagging system in degradation of proteins synthesized from damaged messenger RNA. Science 271:990-993.

54. Lies M., and M. R. Maurizi. 2008. Turnover of endogenous SsrA-tagged proteins mediated by ATP-dependent proteases in *Escherichia coli*. J Biol Chem 283:22918-22929.

55. Moore S. D., and R. T. Sauer. 2007. The tmRNA system for translational surveillance and ribosome rescue. Annu Rev Biochem 76:101-124.

56. Moore S. D., and R. T. Sauer. 2005. Ribosome rescue: tmRNA tagging activity and capacity in *Escherichia coli*. Mol Microbiol 58:456-466.

57. Roche E. D., and R. T. Sauer. 2001. Identification of endogenous SsrA-tagged proteins reveals tagging at positions corresponding to stop codons. J Biol Chem 276: 28509-28515.

58. Bolon D. N., R. A. Grant, T. A. Baker, and R. T. Sauer. 2004. Nucleotide-dependent substrate handoff from the SspB adaptor to the AAA+ ClpXP protease. Mol Cell 16:343-350.

59. Flynn J. M., I. Levchenko, M. Seidel, S. H. Wickner, R. T. Sauer, and T. A. Baker. 2001. Overlapping recognition determinants within the ssrA degradation tag allow modulation of proteolysis. Proc Natl Acad Sci USA 98:10584-10589.

60. McGinness K. E., T. A. Baker, and R. T. Sauer. 2006. Engineering controllable protein degradation. Mol Cell 22:701-707.

61. Levchenko I., M. Seidel, R. T. Sauer, and T. A. Baker. 2000. A specificity-enhancing factor for the ClpXP degradation machine. Science 289:2354-2356.

62. Moore S. D., T. A. Baker, and R. T. Sauer. 2008. Forced extraction of targeted components from complex macromolecular assemblies. Proc Natl Acad Sci USA 105: 11685-11690.

63. Griffith K. L., and A. D. Grossman. 2008. Inducible protein degradation in *Bacillus subtilis* using heterologous peptide tags and adaptor proteins to target substrates to the protease ClpXP. Mol Microbiol 70:1012-1025.

64. Davis J. H., T. A. Baker, and R. T. Sauer. 2009. Engineering synthetic adaptors and substrates for controlled ClpXP degradation. J Biol Chem 284:21848-21855.

65. Farrell C. M., A. D. Grossman, and R. T. Sauer. 2005. Cytoplasmic degradation of ssrAtagged proteins. Mol Microbiol 57:1750-1761.

66. Kenniston J. A., T. A. Baker, and R. T. Sauer. 2005. Partitioning between unfolding and release of native domains during ClpXP degradation determines substrate selectivity and partial processing. Proc Natl Acad Sci USA 102:1390-1395.

67. Lee C., M. P. Schwartz, S. Prakash, M. Iwakura, and A. Matouschek. 2001. ATPdependent proteases degrade their substrates by processively unraveling them from the degradation signal. Mol Cell 7:627-637.

68. Karp P. D., M. Riley, S. M. Paley, and A. Pelligrini-Toole. 1996. EcoCyc: an encyclopedia of *Escherichia coli* genes and metabolism. Nucleic Acids Res 24:32-39.

69. Tatusov R. L., M. Y. Galperin, D. A. Natale, and E. V. Koonin. 2000. The COG database: a tool for genome-scale analysis of protein functions and evolution. Nucleic Acids Res 28:33-36.

70. Moore S. D., and R. T. Sauer. 2008. Revisiting the mechanism of macrolide-antibiotic resistance mediated by ribosomal protein L22. Proc Natl Acad Sci USA 105:18261-18266.

71. Prüß B. M., K. Verma, P. Samanta, P. Sule, S. Kumar, J. Wu, D. Christianson, S. M. Horne, S. J. Stafslien, A. J. Wolfe, and A. Denton. 2010. Environmental and genetic factors that contribute to *Escherichia coli* K-12 biofilm formation. Arch Microbiol.

72. Moore S. D., and P. E. Prevelige. 2001. Structural transformations accompanying the assembly of bacteriophage P22 portal protein rings in vitro. J Biol Chem 276:6779-6788.

73. Moore S. D., and P. E. Prevelige. 2002. Bacteriophage p22 portal vertex formation in vivo. J Mol Biol 315:975-994.

74. Moore S. D., and P. E. Prevelige. 2002. A P22 scaffold protein mutation increases the robustness of head assembly in the presence of excess portal protein. J Virol 76:10245-10255.

75. Gama-Castro S., V. Jiménez-Jacinto, M. Peralta-Gil, A. Santos-Zavaleta, M. I. Peñaloza-Spinola, B. Contreras-Moreira, J. Segura-Salazar, L. Muñiz-Rascado, I. Martinez-Flores, H. Salgado, C. Bonavides-Martínez, C. Abreu-Goodger, C. Rodríguez-Penagos, J. Miranda-Ríos, E. Morett, E. Merino, A. M. Huerta, L. Treviño-Quintanilla, and J. Collado-Vides. 2008. RegulonDB (version 6.0): gene regulation model of *Escherichia coli* K-12 beyond transcription, active (experimental) annotated promoters and Textpresso navigation. Nucleic Acids Res 36:D120-D124.

76. Stein L. D., C. Mungall, S. Shu, M. Caudy, M. Mangone, A. Day, E. Nickerson, J. E. Stajich, T. W. Harris, A. Arva, and S. Lewis. 2002. The generic genome browser: a building block for a model organism system database. Genome Res 12:1599-1610.

77. Abo, T., Inada, T., Ogawa, K., and Aiba, H. (2000) SsrA-mediated tagging and proteolysis of LacI and its role in the regulation of lac operon. EMBO J 19: 3762-3769.

78. Arraiano, C. M., Andrade, J. M., Domingues, S., Guinote, I. B., Malecki, M., Matos, R. G., et al. (2010) The critical role of RNA processing and degradation in the control of gene expression. FEMS Microbiol Rev 34: 883-923.

79. Baker, T. A., and Sauer, R. T. (2011) ClpXP, an ATP-powered unfolding and protein-degradation machine. Biochim Biophys Acta.

80. Bernstein, J. A., Khodursky, A. B., Lin, P. H., Lin-Chao, S., and Cohen, S. N. (2002) Global analysis of mRNA decay and abundance in *Escherichia coli* at single-gene resolution using two-color fluorescent DNA microarrays. Proc Natl Acad Sci USA 99: 9697-9702.

81. Boileau, G., Sommer, A., and Traut, R. R. (1981) Identification of proteins at the binding site for protein S1 in 70 S ribosomes and 30 S subunits by cross-linking with 2-iminothiolane. J Biol Chem 256: 8222-8227.

82. Bollen, A., Lathe, R., Herzog, A., Denicourt, D., Lecocq, J. P., Desmarez, L., and Lavalle, R. (1979) A conditionally lethal mutation of *Escherichia coli* affecting the gene coding for ribosomal protein S2 (rpsB). J Mol Biol 132: 219-233.

83. Boni, I. V., Artamonova, V. S., and Dreyfus, M. (2000) The last RNA-binding repeat of the *Escherichia coli* ribosomal protein S1 is specifically involved in autogenous control. J Bacteriol 182: 5872-5879.

84. Boni, I. V., Isaeva, D. M., Musychenko, M. L., and Tzareva, N. V. (1991) Ribosome-messenger recognition: mRNA target sites for ribosomal protein S1. Nucleic Acids Res 19: 155-162.

85. Briani, F., Curti, S., Rossi, F., Carzaniga, T., Mauri, P., and Dehò, G. (2008) Polynucleotide phosphorylase hinders mRNA degradation upon ribosomal protein S1 overexpression in *Escherichia coli*. RNA 14: 2417-2429.

86. Brock, J. E., Pourshahian, S., Giliberti, J., Limbach, P. A., and Janssen, G. R. (2008) Ribosomes bind leaderless mRNA in *Escherichia coli* through recognition of their 5'-terminal AUG. RNA 14: 2159-2169.

87. Burger, A., Whiteley, C., and Boshoff, A. (2011) Current perspectives of the *Escherichia coli* RNA degradosome. Biotechnol Lett 33: 2337-2350.

88. Charpentier, B., and Branlant, C. (1994) The *Escherichia coli* gapA gene is transcribed by the vegetative RNA polymerase holoenzyme E sigma 70 and by the heat shock RNA polymerase E sigma 32. J Bacteriol 176: 830-839.

89. Cho, B. K., Zengler, K., Qiu, Y., Park, Y. S., Knight, E. M., Barrett, C. L., et al. (2009) The transcription unit architecture of the *Escherichia coli* genome. Nat Biotechnol 27: 1043-1049.

90. Condon, C. (2006) Shutdown decay of mRNA. Mol Microbiol 61: 573-583.

91. Culver, G. M., and Noller, H. F. (1999) Efficient reconstitution of functional *Escherichia coli* 30S ribosomal subunits from a complete set of recombinant small subunit ribosomal proteins. RNA 5: 832-843.

92. Datta, S., Costantino, N., and Court, D. L. (2006) A set of recombineering plasmids for gram-negative bacteria. Gene 379: 109-115.

93. Delvillani, F., Papiani, G., Dello, G., and Briani, F. (2011) S1 ribosomal protein and the interplay between translation and mRNA decay. Nucleic Acids Res.

94. Draper, D. E., and Reynaldo, L. P. (1999) RNA binding strategies of ribosomal proteins. Nucleic Acids Res 27: 381-388.

95. Farwell, M. A., Roberts, M. W., and Rabinowitz, J. C. (1992) The effect of ribosomal protein S1 from *Escherichia coli* and *Micrococcus luteus* on protein synthesis in vitro by *E. coli* and *Bacillus subtilis*. Mol Microbiol 6: 3375-3383.

96. Feng, Y., Huang, H., Liao, J., and Cohen, S. N. (2001) *Escherichia coli* poly(A)-binding proteins that interact with components of degradosomes or impede RNA decay mediated by polynucleotide phosphorylase and RNase E. J Biol Chem 276: 31651-31656.

97. Flynn, J. M., Levchenko, I., Seidel, M., Wickner, S. H., Sauer, R. T., and Baker, T. A. (2001) Overlapping recognition determinants within the ssrA degradation tag allow modulation of proteolysis. Proc Natl Acad Sci USA 98: 10584-10589.

98. Gottesman, S., Roche, E., Zhou, Y., and Sauer, R. T. (1998) The ClpXP and ClpAP proteases degrade proteins with carboxy-terminal peptide tails added by the SsrA-tagging system. Genes Dev 12: 1338-1347.

99. Görke, B., and Stülke, J. (2008) Carbon catabolite repression in bacteria: many ways to make the most out of nutrients. Nat Rev Microbiol 6: 613-624.

100. Griffith, K. L., and Grossman, A. D. (2008) Inducible protein degradation in *Bacillus subtilis* using heterologous peptide tags and adaptor proteins to target substrates to the protease ClpXP. Mol Microbiol 70: 1012-1025.

101. Hayes, C. S., Bose, B., and Sauer, R. T. (2002) Proline residues at the C terminus of nascent chains induce SsrA tagging during translation termination. J Biol Chem 277: 33825-33832.

102. Held, W. A., Mizushima, S., and Nomura, M. (1973) Reconstitution of *Escherichia coli* 30 S ribosomal subunits from purified molecular components. J Biol Chem 248: 5720-5730.

103. Hook-Barnard, I. G., Brickman, T. J., and McIntosh, M. A. (2007) Identification of an AU-rich translational enhancer within the *Escherichia coli* fepB leader RNA. J Bacteriol 189: 4028-4037.

104. JACOB, F., and MONOD, J. (1961) Genetic regulatory mechanisms in the synthesis of proteins. J Mol Biol 3: 318-356.

105. Jones, P. G., Mitta, M., Kim, Y., Jiang, W., and Inouye, M. (1996) Cold shock induces a major ribosomal-associated protein that unwinds double-stranded RNA in *Escherichia coli*. Proc Natl Acad Sci USA 93: 76-80.

106. Kaberdina, A. C., Szaflarski, W., Nierhaus, K. H., and Moll, I. (2009) An unexpected type of ribosomes induced by kasugamycin: a look into ancestral times of protein synthesis? Mol Cell 33: 227-236.

107. Kalapos, M. P., Paulus, H., and Sarkar, N. (1997) Identification of ribosomal protein S1 as a poly(A) binding protein in *Escherichia coli*. Biochimie 79: 493-502.

108. Kenniston, J. A., Baker, T. A., and Sauer, R. T. (2005) Partitioning between unfolding and release of native domains during ClpXP degradation determines substrate selectivity and partial processing. Proc Natl Acad Sci USA 102: 1390-1395.

109. Kingston, R. E., Chomczynski, P., and Sacchi, N. (2001) Guanidine methods for total RNA preparation. Curr Protoc Mol Biol Chapter 4: Unit4.2.

110. Kitakawa, M., and Isono, K. (1982) An amber mutation in the gene rpsA for ribosomal protein S1 in *Escherichia coli*. Mol Gen Genet 185: 445-447.

111. Lee, C., Schwartz, M. P., Prakash, S., Iwakura, M., and Matouschek, A. (2001) ATP-dependent proteases degrade their substrates by processively unraveling them from the degradation signal. Mol Cell 7: 627-637.

112. Lies, M., and Maurizi, M. R. (2008) Turnover of endogenous SsrA-tagged proteins mediated by ATP-dependent proteases in *Escherichia coli*. J Biol Chem 283: 22918-22929.

113. Malys, N., and McCarthy, J. E. (2011) Translation initiation: variations in the mechanism can be anticipated. Cell Mol Life Sci 68: 991-1003.

114. Martin, A., Baker, T. A., and Sauer, R. T. (2008) Pore loops of the AAA+ ClpX machine grip substrates to drive translocation and unfolding. Nat Struct Mol Biol 15: 1147-1151.

115. McGinness, K. E., Baker, T. A., and Sauer, R. T. (2006) Engineering controllable protein degradation. Mol Cell 22: 701-707.

116. Mendoza-Vargas, A., Olvera, L., Olvera, M., Grande, R., Vega-Alvarado, L., Taboada, B., et al. (2009) Genome-wide identification of transcription start sites, promoters and transcription factor binding sites in *E. coli*. PLoS One 4: e7526.

117. Moll, I., and Bläsi, U. (2002) Differential inhibition of 30S and 70S translation initiation complexes on leaderless mRNA by kasugamycin. Biochem Biophys Res Commun 297: 1021-1026.

118. Moll, I., Grill, S., Grundling, A., and Bläsi, U. (2002a) Effects of ribosomal proteins S1, S2 and the DeaD/CsdA DEAD-box helicase on translation of leaderless and canonical mRNAs in *Escherichia coli*. Mol Microbiol 44: 1387-1396.

119. Moll, I., Grill, S., Gualerzi, C. O., and Bläsi, U. (2002b) Leaderless mRNAs in bacteria: surprises in ribosomal recruitment and translational control. Mol Microbiol 43: 239-246.
120. Monod, J. (1949) The Growth of Bacterial Cultures. Annual Reviews of Microbiology 3: 371-394.
121. Moore, S. D. (2011) Assembling new *Escherichia coli* strains by transduction using phage P1. Methods Mol Biol 765: 155-169.
122. Moore, S. D., Baker, T. A., and Sauer, R. T. (2008) Forced extraction of targeted components from complex macromolecular assemblies. Proc Natl Acad Sci USA 105: 11685-11690.
123. Nakagawa, S., Niimura, Y., Miura, K., and Gojobori, T. (2010) Dynamic evolution of translation initiation mechanisms in prokaryotes. Proc Natl Acad Sci USA 107: 6382-6387.
124. Oehler, S. (2009) Feedback regulation of Lac repressor expression in *Escherichia coli*. J Bacteriol 191: 5301-5303.
125. Peil, L., Virumäe, K., and Remme, J. (2008) Ribosome assembly in *Escherichia coli* strains lacking the RNA helicase DeaD/CsdA or DbpA. FEBS J 275: 3772-3782.
126. Phadtare, S., and Severinov, K. (2010) RNA remodeling and gene regulation by cold shock proteins. RNA Biol 7: 788-795.
127. Portier, C., and Regnier, P. (1984) Expression of the rpsO and pnp genes: structural analysis of a DNA fragment carrying their control regions. Nucleic Acids Res 12: 6091-6102.
128. Prud'homme-Généreux, A., Beran, R. K., Iost, I., Ramey, C. S., Mackie, G. A., and Simons, R. W. (2004) Physical and functional interactions among RNase E, polynucleotide phosphorylase and the cold-shock protein, CsdA: evidence for a 'cold shock degradosome'. Mol Microbiol 54: 1409-1421.
129. Py, B., Higgins, C. F., Krisch, H. M., and Carpousis, A. J. (1996) A DEAD-box RNA helicase in the *Escherichia coli* RNA degradosome. Nature 381: 169-172.
130. Raghavan, R., Sage, A., and Ochman, H. (2011) Genome-wide identification of transcription start sites yields a novel thermosensing RNA and new cyclic AMP receptor protein-regulated genes in *Escherichia coli*. J Bacteriol 193: 2871-2874.
131. Rasmussen, M. D., Sørensen, M. A., and Pedersen, S. (1993) Isolation and characterization of mutants with impaired regulation of rpsA, the gene encoding ribosomal protein S1 of *Escherichia coli*. Mol Gen Genet 240: 23-28.
132. Régnier, P., and Hajnsdorf, E. (1991) Decay of mRNA encoding ribosomal protein S15 of *Escherichia coli* is initiated by an RNase E-dependent endonucleolytic cleavage that removes the 3' stabilizing stem and loop structure. J Mol Biol 217: 283-292.
133. Ruijter, J. M., Ramakers, C., Hoogaars, W. M., Karlen, Y., Bakker, O., van den Hoff, M. J., and Moorman, A. F. (2009) Amplification efficiency: linking baseline and bias in the analysis of quantitative PCR data. Nucleic Acids Res 37: e45.
134. Seta, F. D., Boschi-Muller, S., Vignais, M. L., and Branlant, G. (1997) Characterization of *Escherichia coli* strains with gapA and gapB genes deleted. J Bacteriol 179: 5218-5221.
135. Shajani, Z., Sykes, M. T., and Williamson, J. R. (2011) Assembly of bacterial ribosomes. Annu Rev Biochem 80: 501-526.
136. Sharan, S. K., Thomason, L. C., Kuznetsov, S. G., and Court, D. L. (2009) Recombineering: a homologous recombination-based method of genetic engineering. Nat Protoc 4: 206-223.
137. Shultzaberger, R. K., Bucheimer, R. E., Rudd, K. E., and Schneider, T. D. (2001) Anatomy of *Escherichia coli* ribosome binding sites. J Mol Biol 313: 215-228.
138. Skorski, P., Leroy, P., Fayet, O., Dreyfus, M., and Hermann-Le Denmat, S. (2006) The highly efficient translation initiation region from the *Escherichia coli* rpsA gene lacks a shine-dalgarno element. J Bacteriol 188: 6277-6285.
139. Skouv, J., Schnier, J., Rasmussen, M. D., Subramanian, A. R., and Pedersen, S. (1990) Ribosomal protein S1 of *Escherichia coli* is the effector for the regulation of its own synthesis. J Biol Chem 265: 17044-17049.
140. Sorokin, A., Senor, P., Pujic, P., Azevedo, V., and Ehrlich, S. D. (1995) The *Bacillus subtilis* chromosome region encoding homologues of the *Escherichia coli* mssA and rpsA gene products. Microbiology 141 (Pt 2): 311-319.
141. Studier, F. W. (2005) Protein production by auto-induction in high density shaking cultures. Protein Expr Purif 41: 207-234.
142. Subramanian, A. R. (1983) Structure and functions of ribosomal protein S1. Prog Nucleic Acid Res Mol Biol 28: 101-142.
143. Suryanarayana, T., and Subramanian, A. R. (1983) An essential function of ribosomal protein S1 in messenger ribonucleic acid translation. Biochemistry 22: 2715-2719.
144. Sørensen, M. A., Fricke, J., and Pedersen, S. (1998) Ribosomal protein S1 is required for translation of most, if not all, natural mRNAs in *Escherichia coli* in vivo. J Mol Biol 280: 561-569.
145. Tedin, K., Resch, A., and Bläsi, U. (1997) Requirements for ribosomal protein S1 for translation initiation of mRNAs with and without a 5' leader sequence. Mol Microbiol 25: 189-199.
146. Thouvenot, B., Charpentier, B., and Branlant, C. (2004) The strong efficiency of the *Escherichia coli* gapA P1 promoter depends on a complex combination of functional determinants. Biochem J 383: 371-382.
147. Toone, W. M., Rudd, K. E., and Friesen, J. D. (1991) deaD, a new *Escherichia coli* gene encoding a presumed ATP-dependent RNA helicase, can suppress a mutation in rpsB, the gene encoding ribosomal protein S2. J Bacteriol 173: 3291-3302.
148. Uliczka, F., Pisano, F., Kochut, A., Opitz, W., Herbst, K., Stolz, T., and Dersch, P. (2011) Monitoring of Gene Expression in Bacteria during Infections Using an Adaptable Set of Bioluminescent, Fluorescent and Colorigenic Fusion Vectors. PLoS One 6: e20425.
149. Vesper, O., Amitai, S., Belitsky, M., Byrgazov, K., Kaberdina, A. C., Engelberg-Kulka, H., and Moll, I. (2011) Selective translation of leaderless mRNAs by specialized ribosomes generated by MazF in *Escherichia coli*. Cell 147: 147-157.
150. Xu, L., Lv, J., Lin, L., Wang, P., Song, P., Su, R., and Zhu, G. (2011) Altered nucleic acid partitioning during phenol extraction or silica adsorption by guanidinium and potassium salts. Anal Biochem.
151. Yamaguchi, Y., and Inouye, M. (2009) mRNA interferases, sequence-specific endoribonucleases from the toxin-antitoxin systems. Prog Mol Biol Transl Sci 85: 467-500.
152. Yoder-Himes, D. R., Chain, P. S., Zhu, Y., Wurtzel, O., Rubin, E. M., Tiedje, J. M., and Sorek, R. (2009) Mapping the Burkholderia cenocepacia niche response via high-throughput sequencing. Proc Natl Acad Sci USA 106: 3976-3981.
153. Zuker, M. (2003) Mfold web server for nucleic acid folding and hybridization prediction. Nucleic Acids Res 31: 3406-3415.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding of the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A construct for making a fusion protein, comprising:
   (i) a nucleotide sequence encoding a degradation tag having a ClpX binding sequence comprising SEQ ID NO:4 for a ClpXP protease, wherein the nucleotide sequence does not encode a binding sequence for at least one of ClpA and SspB,
   (ii) an antibiotic resistance marker, and
   (iii) flanking sequences, wherein the flanking sequences comprise recognition sequences that correspond to sequences of a gene encoding a target protein.

2. The construct of claim 1, wherein the nucleotide sequence encoding the degradation tag further encodes a detection marker, a purification marker, or both.

3. The construct of claim 1, wherein the nucleotide sequence encoding the degradation tag further encodes a FLAG epitope, a His6 epitope, or a combination thereof.

4. A method of controlling degradation of a target protein, the method comprising:
   expressing a fusion protein in a host cell, wherein the host cell comprises a ClpXP protease activity with respect to the expressed fusion protein, wherein the fusion protein comprises a target protein endogenous to the host cell and a degradation tag having a ClpX binding sequence comprising SEQ ID NO:4 for a ClpXP protease, and wherein the fusion protein does not bind at least one of ClpA and SspB.

5. The method of claim 4, wherein the target protein is S1 and wherein the host cell is *E. coli*.

6. The method of claim 4, wherein the fusion protein further comprises a FLAG epitope.

7. The method of claim 4, wherein the fusion protein further comprises a $His_6$ epitope.

8. The method of claim 4, wherein expressing the fusion protein comprises:
   providing to the host cell a genetic construct comprising (i) a nucleotide sequence encoding the degradation tag having the ClpX binding sequence comprising SEQ ID NO:4 for the ClpXP protease and (ii) flanking sequences, wherein the flanking sequences comprise recognition sequences that correspond to sequences of the gene encoding the target protein;
   inserting into an open reading frame of the gene encoding the target protein the genetic construct; and
   expressing the genetic construct.

9. The method of claim 8, wherein the flanking sequences direct recombination to the 3' end of the gene encoding the target protein.

10. The method of claim 4, wherein the fusion protein further comprises a linker.

11. The method of claim 4, wherein the fusion protein further comprises an antibiotic resistance marker.

12. The method of claim 11, wherein the antibiotic resistance marker is kanR, tetR, or ampR.

13. The method of claim 4, wherein the fusion protein further comprises a FLAG epitope, a $His_6$ epitope, an antibiotic resistance marker or a combination thereof.

14. The method of claim 8, wherein the construct further comprises nucleotide sequences for a linker.

15. The method of claim 8, wherein the construct further comprises (iii) nucleotide sequences for an antibiotic resistance marker.

16. The method of claim 15, wherein the antibiotic resistance marker is kanR, tetR, or ampR.

17. The method of claim 8, wherein the construct further comprises (iii) a nucleotide sequence for a FLAG epitope.

18. The method of claim 8, wherein the construct further comprises (iii) a nucleotide sequence for $His_6$ epitope.

19. The method of claim 8, wherein the construct further comprises (iii) nucleotide sequences for a FLAG epitope, a $His_6$ epitope, an antibiotic resistance marker or a combination thereof.

* * * * *

```
                         SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: synthetic construct; ssrA degradation tag
      containing SspB binding sequence and Clp X binding sequence

<400> SEQUENCE: 1

Ala Ala Asn Asp Glu Asn Tyr Ala Leu Ala Ala
1               5                   10

<210> SEQ ID NO 2
<211> LENGTH: 26
<212> TYPE: PRT
<213> ORGANISM: Artificial Sequence
<220> FEATURE:
<223> OTHER INFORMATION: synthetic construct; degradation tag containing
      FLAG tag, Histidine tag and ClpX binding sequence

<400> SEQUENCE: 2

Gly Gly Ser Asp Tyr Lys Asp Asp Asp Lys Gly His His His His
1               5                   10                  15

His His Gly Ser Thr Tyr Ala Leu Ala Ala
            20                  25

<210> SEQ ID NO 3
<211> LENGTH: 18
<212> TYPE: PRT
<213> ORGANISM: Artificial Sequence
<220> FEATURE:
<223> OTHER INFORMATION: synthetic construct; control tag containing
      FLAG tag and histidine tag

<400> SEQUENCE: 3

Gly Gly Ser Asp Tyr Lys Asp Asp Asp Lys Gly His His His His
1               5                   10                  15

His His
```

```
<210> SEQ ID NO 4
<211> LENGTH: 5
<212> TYPE: PRT
<213> ORGANISM: Artificial Sequence
<220> FEATURE:
<223> OTHER INFORMATION: synthetic construct; ClpX binding sequence

<400> SEQUENCE: 4

Tyr Ala Leu Ala Ala
1               5
```